US007718772B2

(12) United States Patent
Mattson et al.

(10) Patent No.: US 7,718,772 B2
(45) Date of Patent: May 18, 2010

(54) CANINE THYMIC STROMAL LYMPHOPOIETIN PROTEIN AND USES THEREOF

(75) Inventors: Jeanine D. Mattson, San Francisco, CA (US); Daniel M. Gorman, Palo Alto, CA (US); Rene de Waal Malefyt, Sunnyvale, CA (US); Mohamad A. Morsey, Omaha, NE (US)

(73) Assignee: Schering-Plough Animal Health Corporation, Summit, NJ (US)

( * ) Notice: Subject to any disclaimer, the term of this patent is extended or adjusted under 35 U.S.C. 154(b) by 0 days.

(21) Appl. No.: 11/954,143

(22) Filed: Dec. 11, 2007

(65) Prior Publication Data

US 2008/0152620 A1 Jun. 26, 2008

Related U.S. Application Data

(60) Provisional application No. 60/875,135, filed on Dec. 14, 2006.

(51) Int. Cl.
| | | |
|---|---|---|
| C07K 1/00 | (2006.01) | |
| C07K 14/00 | (2006.01) | |
| C07K 17/00 | (2006.01) | |
| C07K 2/00 | (2006.01) | |
| C07K 4/00 | (2006.01) | |
| C07K 5/00 | (2006.01) | |
| C07K 7/00 | (2006.01) | |
| C07K 16/00 | (2006.01) | |
| A61K 38/00 | (2006.01) | |
| A61K 45/00 | (2006.01) | |
| A61K 39/00 | (2006.01) | |
| A01N 37/18 | (2006.01) | |

(52) U.S. Cl. .......................... 530/350; 530/300; 514/2; 424/85.2; 424/185.1
(58) Field of Classification Search ...................... None
See application file for complete search history.

(56) References Cited

U.S. PATENT DOCUMENTS

| | | | |
|---|---|---|---|
| 4,281,061 | A | 7/1981 | Zuk et al. |
| 5,627,043 | A | 5/1997 | Franzusoff |
| 5,965,122 | A | 10/1999 | Namen et al. |
| 6,555,520 | B2 | 4/2003 | Sims et al. |
| 6,844,170 | B1 | 1/2005 | Moore et al. |
| 7,304,144 | B2 | 12/2007 | Sims et al. |
| 2002/0068323 | A1 | 6/2002 | Saris et al. |
| 2002/0173623 | A1 | 11/2002 | Reche-Gallardo et al. |
| 2003/0099947 | A1 | 5/2003 | Bazan et al. |
| 2006/0223754 | A1 | 10/2006 | Sims et al. |

FOREIGN PATENT DOCUMENTS

| | | |
|---|---|---|
| EP | 0314415 A2 | 5/1989 |
| WO | WO 00/29581 | 5/2000 |
| WO | WO 00/39149 | 7/2000 |

OTHER PUBLICATIONS

Bendayan, M., "Possibilities of False Immunocytochemical Results Generated by The Use of Monoclonal Antibodies: The Example of the Anti-proinsulin Antibody," The Journal of Histochemistry and Cytochemistry, vol. 43(9) pp. 881-886 (1995).
Bost, K., et al., "Antibodies Against a Peptide Sequence Within The HIV Envelope Protein Cross reacts with Human Interleukin-2," Immunological Investigations, vol. 17(6&7), pp. 577-586 (1988).
Carpino, N., et al., "Absence of an Essential Role for Thymic Stromal Lymphopoietin Receptor in Murine B-Cell Development," Molecular and Cellular Biology, vol. 24(6), pp. 2584-2592 (2004).
Fry, T., et al., "Interleukin-7: from bench to clinic," Blood, vol. 99 (11) pp. 3892-3904 (2002).
Gavilondo, J., et al., "Antibody Engineering at the Millennium," BioTechniques, vol. 29, pp. 128-145 (2000).
Gilliet, M., et al., "Human Dendritic Cells Activated by TSLP and CD40L Induce Proallergic Cytotoxic T Cells," J. Exp. Med., vol. 197(8), pp. 1059-1063 (2003).
Isaksen, D., et al.,"Requirement for Stat5 in Thymic Stromal Lymphopoietin-Mediated Signal Transduction1," The Journal of Immunology, vol. 163, pp. 5971-5977 (1999).
Janeway, C., "The Immune System in Health and Disease," Garland Science, 3$^{rd}$ Edition, pp. A:11 (1997).
Leonard, W., et al., "TSLP: finally in the limelight," Nature Immunology, vol. 3(7) pp. 605-607 (2002).
Liu, Y., "TSLP: An Epithelial Cell Cytokine that Regulates T Cell Differentiation by Conditioning Dendritic Cell Maturation," Ann. Rev. Immunol. vol. 25 pp. 193-219 (2007).
Liu, Y., "Thymic stromal lymphopoietin: master switch for allergic inflammation," The Journal of Experimental Medicine, vol. 203(2), pp. 269-273 (2006).
Park, L., et al., "Cloning of the Murine Thymic Stromal Lymphopoietin (TSLP) Receptor: Formation of a Functional Heteromeric Complex Requires Interleukin 7 Receptor," The Journal of Experimental Medicine, vol. 192(5), pp. 659-669 (2000).
Ray, R., et al., "Characterization of thymic stromal-derived lymphopoietin (TSLP) in murine B cell development in vitro," Eur. J. Immunol. vol. 26, pp. 10-16 (1996).
Reche, P., et al., "Human Thymic Stromal Lymphopoietin Preferentially Stimulates Myeloid Cells," The Journal of Immunology, vol. 167, pp. 336-343 (2001).
Rochman, I., et al., "Cutting Edge: Direct Action of Thymic Stromal Lymphopoietin on Activated Human CD4$^+$ T Cells", The Journal of Immunology, vol. 178 pp. 6720-6724 (2007).
Sims, J., et al., "Molecular Cloning and Biological Characterization of a Novel Murine Lymphoid Growth Factor", The Journal of Experimental Medicine, vol. 192, No. 5, pp. 671-680 (2000).

(Continued)

Primary Examiner—Robert Landsman

(57) ABSTRACT

The present invention discloses a canine TSLP protein and a nucleic acid that encodes that protein. Peptide fragments of the protein that comprise specific epitopes of the canine TSLP protein are also disclosed. The canine TSLP protein and related peptide fragments may be used as an antigen for immunological assays, as well as for vaccines that induce anti-TSLP antibodies. The present invention further discloses methods of making and using the canine TSLP gene, the canine TSLP protein, and the related peptide fragments.

18 Claims, 8 Drawing Sheets

OTHER PUBLICATIONS

Soumelis, V., et al., "Human epithelial cells trigger dendritic cell-mediated allergic inflammation by producing TSLP," Nature Immunology, vol. 3(7), pp. 673-680 (2002).

Soumelis, V., et al., "Human thymic stromal lymphopoietin: a novel epithelial cell-derived cytokine and a potential key player in the induction of allergic inflammation," Springer Semi Immun., vol. 25, pp. 325-333 (2004).

Voβhenrich, C., et al., "Thymic stromal-derived lymphopoietin distinguishes fetal from adult B cell development," Nature Immunology, vol. 4(8) pp. 773-779 (2003).

Wang, J., et al., "Human TSLP-Educated DCs," Cellular & Molecular Immunology, vol. 5(2), pp. 99-106 (2008).

Watanabe, N., et al., "Human TSLP promotes CD40 ligand-induced IL-12 production by myeloid dendritic cells but maintains their Th2 priming potential," Blood, vol. 105(12) pp. 4749-4751 (2005).

Watanabe, N., et al., "Human thymic stromal lymphopoietin promotes dendritic cell-mediated CD4+ T cell homeostatic expansion," Nature Immunology, vol. 5(4) pp. 426-434 (2005).

Zhou, B., et al., "Thymic stromal lymphopoietin as a key initiator of allergic airway inflammation in mice," Nature Immunology, vol. 6(10) pp. 1047-1053 (2005).

Ziegler, S., et al. "Thymic stromal lymphopoietin in normal and pathogenic T cell development and function," Nature Immunology, vol. 7(7), pp. 709-714 (2006).

Valenzona et al., "Exogenous Interleukin 7 as a Proliferative Stimulant of Early Precursor B Cells in Mouse Bone Marrow: Efficacy of IL-7 Injection, IL-7 Infusion and IL-7-Anti-IL-7 Antibody Complexes," Cytokine, vol. 10, No. 6, pp. 404-412 (Jun. 1998).

Miyaji, et al., "A Comparison of Proliferative Response to IL-7 and Expression of IL-7 Receptors in Intermediate TCR Cells of the Liver, Spleen, and Thymus," Cellular Immunology vol. 169, Article 0106, pp. 159-165 (1996).

Pearson, et al., "Effective Protein Sequence Comparison," Methods in Enzymology, vol. 266, pp. 227-258 (1996).

Mott, et al., "Four-Helix Bundle Growth Factors and Their Receptors: Protein-Protein Interactions," Current Opinion in Structural Biology, vol. 5, No. 1, pp. 114-121 (1995).

Kroemer, et al., "Prediction of the Three-Dimensional Structure of Human Interleukin-7 by Homology Modeling," Protein Engineering, vol. 9, No. 6, pp. 493-498 (1996).

Winkler, et al., "Interleukin-3 and Interleukin-7 Are Alternative Growth Factors for the Same B-Cell Precursors in the Mouse," Blood, vol. 85, pp. 2045-2051 (1995).

Al-Shami, et al., "A Role for Thymic Stromal Lymphopoietin in CD4+ T Cell Development," The Journal of Experimental Medicine, vol. 200, No. 2, pp. 159-168 (2004).

Cosenza, et al., "Disulfide Bond Assignment in Human Interleukin-7 by Matrix-Assisted Laser Desorption/Ionization Mass Spectroscopy and Site-Directed Cysteine to Serine Mutational Analysis," The Journal of Biological Chemistry, vol. 272, No. 52, pp. 32995-33000 (1997).

Kruse, et al., "Two Distinct Functional Sites of Human Interleukin 4 Are Identified by Variants Impaired in Either Receptor Binding or Receptor Activation," The EMBO Journal, vol. 12, No. 13, pp. 5121-5129 (1993).

Levin, Steven D., et al., Journal of Immunology, "Thymic Stromal Lymphoprotein: A cytokine that promotes the development of IgM+ B cells in Vitro and Signals via a novel mechanism," (Jan. 1999), pp. 677-683, vol. 162.

Mahairas, G.G., et al., GenBank, Accession No. AQ781833, (Aug. 2, 1999), Definition: "HS_3148_A2_C03_T7C CIT Approved Human Genomic Sperm Library D Homo sapiens genomic clone Plate=3148 Col=6 Row=E, genomic survey sequence."

Maeurer, Markus J., et al., The Cytokine Handbook, 3rd ed., "Interleukin-7," (1998), Ch. 9:229-269. Thomson, ed.(Acadennic Press, Inc., San Diego, California).

Marra, M., et al., GenBank, Accession No. AA717930, (Dec. 29, 1997), Definition: "vt09f05.r1 Barstead mouse myotubes MPLRB5 Mus musculus cDNA clone Image: 1162593 5', mRNA sequence."

Marra, M., et al., GenBank, Accession No. AI591430, (Apr. 21, 1999), Definition: "vt09f05.r1 Barstead mouse myotubes MPLRB5 Mus musculus cDNA clone Image: 1162593 5', mRNA sequence."

NCI-CGAP. GenBank, Accession No. AA889581, (Jan. 4, 1999), Definition: "ak25a11.sl Soares_testis_NHT Homo sapiens cDNA clone Image: 14072603', mRNA sequence."

International Search Report for application No. PCT/US99/20871 (6 pages) (DX0903K).

Osborn, et al., "Overexpression of Murine TSLP Impairs Lymphopoiesis and Myelopoiesis," Blood, vol. 103, No. 3, pp. 843-851 (2004).

Quentmeier, et al., "Cloning of Human Thymic Stromal Lymphopoietin (TSLP) and Signaling Mechanisms Leading to Proliferation," Leukemia, vol. 15, No. 8, pp. 1286-1292 (2001).

Friend, Sherree Lee, et al., Experimental Hematology, "A thymic stromal cell line supports in vitro development of surface IgM+ B cells and produces a novel growth factor affecting B and T lineage cells" (1994), pp. 321-328, vol. 3.

Busse, W., et al., "Advances in Immunology", The New England Journal of Medicine, vol. 344, No. 5, pp. 350-362 (2001).

Holgate, S., "Allergic Disorders", British Medical Journal, vol. 320, pp. 231-234 (2000).

Renauld, J-C., "New Insights into the role of cytokines in asthma", Journal of Clinical Pathology, vol. 54, pp. 577-589 (2001).

Liu, Yong-Jun et al., "TSLP: An Epithelial Cell Cytokine that Regulates T Cell Differentiation by Conditioning Dendritic Cell Maturation", *Annu. Rev. Immunol.*, 25:193-219 (2007).

FIG. 7

Dog:      ARIERLTLHRIRGCA
human:    TEIQSLTFNPTAGCA

FIG. 8A

```
5'-
ATGGTGCCTGATGCCCTGCTGAGCGTGCTGAGCGTGTTCTTTAGGAAGAT
CTTCGTCTTGCAGCTGGTAGGGCTGGTGCTAACCTACAATTTCATTGACT
GTGACTTTGAGAAGATTAGATGGAAGTATCAGGAAGTCATTTACCAAGCC
CTGGAGAAATACATGGATGGGACCAGGAGCACGGAGTTCAGCCACCCCGT
GTACTGCGCGAACCCGCCCGACTGCCTGGCCAGGATCGAGCGGCTCACCC
TGCACCGCATCCGCGGCTGCGCGTCGGGCGCCCGGGAGGCCTTCGCCGAG
GGGACGGTCGCCGCGCTCGCCGCCGAGTGCCCGGGCTACGCCGCAGCGCC
GATAAATAATACCCAGGCAAAGAAGAAAGAAAAAAAGAGGAGTCACAA
CAAATAAATGCCGGGAACAAGTCGCACACTTAATAGGGCTGTGGCGTCGT
TTCAGTCGCATTTCATAG  -3'
```

MVPDALLSVLSVFFRKIFVLQLVGLVLTYNFIDCDFEKIRWKYQEVIYQA
LEKYMDGTRSTEFSHPVYCANPPDCLARIERLTLHRIRGCASGAREAFAE
GTVAALAAECPGYAAAPINNTQAKKKRKKRGVTTNKCREQVAHLIGLWRR
FSRIS

SEQUENCE LISTING

<160> NUMBER OF SEQ ID NOS: 118

<210> SEQ ID NO 1
<211> LENGTH: 468
<212> TYPE: DNA
<213> ORGANISM: Canis familiaris

<400> SEQUENCE: 1

```
atggtgcctg atgccctgct gagcgtgctg agcgtgttct ttaggaagat cttcgtcttg    60
cagctggtag ggctggtgct aacctacaat ttcattgact gtgactttga gaagattaga   120
tggaagtatc aggaagtcat ttaccaagcc ctggagaaat acatggatgg gaccaggagc   180
acggagttca gccaccccgt gtactgcgcg aacccgcccg actgcctggc caggatcgag   240
cggctcaccc tgcaccgcat ccgcggctgc gcgtcgggcg cccgggaggc cttcgccgag   300
gggacggtcg ccgcgctcgc cgccgagtgc ccgggctacg ccgcagcgcc gataaataat   360
acccaggcaa agaagaaaag aaaaaaaaga ggagtcacaa caaataaatg ccgggaacaa   420
gtcgcacact taatagggct gtggcgtcgt ttcagtcgca tttcatag                 468
```

<210> SEQ ID NO 2
<211> LENGTH: 155
<212> TYPE: PRT
<213> ORGANISM: Canis familiaris

<400> SEQUENCE: 2

```
Met Val Pro Asp Ala Leu Leu Ser Val Leu Ser Val Phe Phe Arg Lys
1               5                   10                  15

Ile Phe Val Leu Gln Leu Val Gly Leu Val Leu Thr Tyr Asn Phe Ile
            20                  25                  30
```

```
Asp Cys Asp Phe Glu Lys Ile Arg Trp Lys Tyr Gln Glu Val Ile Tyr
        35                  40                  45

Gln Ala Leu Glu Lys Tyr Met Asp Gly Thr Arg Ser Thr Glu Phe Ser
 50                  55                  60

His Pro Val Tyr Cys Ala Asn Pro Pro Asp Cys Leu Ala Arg Ile Glu
 65                  70                  75                  80

Arg Leu Thr Leu His Arg Ile Arg Gly Cys Ala Ser Gly Ala Arg Glu
                 85                  90                  95

Ala Phe Ala Glu Gly Thr Val Ala Ala Leu Ala Glu Cys Pro Gly
            100                 105                 110

Tyr Ala Ala Pro Ile Asn Asn Thr Gln Ala Lys Lys Lys Arg Lys
            115                 120                 125

Lys Arg Gly Val Thr Thr Asn Lys Cys Arg Glu Gln Val Ala His Leu
130                 135                 140

Ile Gly Leu Trp Arg Arg Phe Ser Arg Ile Ser
145                 150                 155

<210> SEQ ID NO 3
<211> LENGTH: 15
<212> TYPE: PRT
<213> ORGANISM: Homo sapiens

<400> SEQUENCE: 3

Thr Glu Ile Gln Ser Leu Thr Phe Asn Pro Thr Ala Gly Cys Ala
 1               5                  10                  15

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aataatccat ggcatacaat ttcattgact gtgac                              35

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaaatagata tctgaaatgc gactgaaacg acg                                33

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aataatccat ggcatacaat ttcattgact gtgac                              35

<210> SEQ ID NO 7
<211> LENGTH: 33
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
acataaaagc tttgaaatgc gactgaaacg acg                                      33

<210> SEQ ID NO 8
<211> LENGTH: 15
<212> TYPE: PRT
<213> ORGANISM: Canis familiaris

<400> SEQUENCE: 8

Tyr Asn Phe Ile Asp Cys Asp Phe Glu Lys Ile Arg Trp Lys Tyr
1               5                   10                  15

<210> SEQ ID NO 9
<211> LENGTH: 15
<212> TYPE: PRT
<213> ORGANISM: Canis familiaris

<400> SEQUENCE: 9

Phe Ile Asp Cys Asp Phe Glu Lys Ile Arg Trp Lys Tyr Gln Glu
1               5                   10                  15

<210> SEQ ID NO 10
<211> LENGTH: 15
<212> TYPE: PRT
<213> ORGANISM: Canis familiaris

<400> SEQUENCE: 10

Asp Cys Asp Phe Glu Lys Ile Arg Trp Lys Tyr Gln Glu Val Ile
1               5                   10                  15

<210> SEQ ID NO 11
<211> LENGTH: 15
<212> TYPE: PRT
<213> ORGANISM: Canis familiaris

<400> SEQUENCE: 11

Asp Phe Glu Lys Ile Arg Trp Lys Tyr Gln Glu Val Ile Tyr Gln
1               5                   10                  15

<210> SEQ ID NO 12
<211> LENGTH: 15
<212> TYPE: PRT
<213> ORGANISM: Canis familiaris

<400> SEQUENCE: 12

Glu Lys Ile Arg Trp Lys Tyr Gln Glu Val Ile Tyr Gln Ala Leu
1               5                   10                  15

<210> SEQ ID NO 13
<211> LENGTH: 15
<212> TYPE: PRT
<213> ORGANISM: Canis familiaris

<400> SEQUENCE: 13

Ile Arg Trp Lys Tyr Gln Glu Val Ile Tyr Gln Ala Leu Glu Lys
1               5                   10                  15

<210> SEQ ID NO 14
<211> LENGTH: 15
<212> TYPE: PRT
```

-continued

<213> ORGANISM: Canis familiaris

<400> SEQUENCE: 14

Trp Lys Tyr Gln Glu Val Ile Tyr Gln Ala Leu Glu Lys Tyr Met
1               5                   10                  15

<210> SEQ ID NO 15
<211> LENGTH: 15
<212> TYPE: PRT
<213> ORGANISM: Canis familiaris

<400> SEQUENCE: 15

Tyr Gln Glu Val Ile Tyr Gln Ala Leu Glu Lys Tyr Met Asp Gly
1               5                   10                  15

<210> SEQ ID NO 16
<211> LENGTH: 15
<212> TYPE: PRT
<213> ORGANISM: Canis familiaris

<400> SEQUENCE: 16

Glu Val Ile Tyr Gln Ala Leu Glu Lys Tyr Met Asp Gly Thr Arg
1               5                   10                  15

<210> SEQ ID NO 17
<211> LENGTH: 15
<212> TYPE: PRT
<213> ORGANISM: Canis familiaris

<400> SEQUENCE: 17

Ile Tyr Gln Ala Leu Glu Lys Tyr Met Asp Gly Thr Arg Ser Thr
1               5                   10                  15

<210> SEQ ID NO 18
<211> LENGTH: 15
<212> TYPE: PRT
<213> ORGANISM: Canis familiaris

<400> SEQUENCE: 18

Gln Ala Leu Glu Lys Tyr Met Asp Gly Thr Arg Ser Thr Glu Phe
1               5                   10                  15

<210> SEQ ID NO 19
<211> LENGTH: 15
<212> TYPE: PRT
<213> ORGANISM: Canis familiaris

<400> SEQUENCE: 19

Leu Glu Lys Tyr Met Asp Gly Thr Arg Ser Thr Glu Phe Ser His
1               5                   10                  15

<210> SEQ ID NO 20
<211> LENGTH: 15
<212> TYPE: PRT
<213> ORGANISM: Canis familiaris

<400> SEQUENCE: 20

Lys Tyr Met Asp Gly Thr Arg Ser Thr Glu Phe Ser His Pro Val
1               5                   10                  15

<210> SEQ ID NO 21
<211> LENGTH: 15
<212> TYPE: PRT
<213> ORGANISM: Canis familiaris

```
<400> SEQUENCE: 21

Met Asp Gly Thr Arg Ser Thr Glu Phe Ser His Pro Val Tyr Cys
1               5                   10                  15

<210> SEQ ID NO 22
<211> LENGTH: 15
<212> TYPE: PRT
<213> ORGANISM: Canis familiaris

<400> SEQUENCE: 22

Gly Thr Arg Ser Thr Glu Phe Ser His Pro Val Tyr Cys Ala Asn
1               5                   10                  15

<210> SEQ ID NO 23
<211> LENGTH: 15
<212> TYPE: PRT
<213> ORGANISM: Canis familiaris

<400> SEQUENCE: 23

Arg Ser Thr Glu Phe Ser His Pro Val Tyr Cys Ala Asn Pro Pro
1               5                   10                  15

<210> SEQ ID NO 24
<211> LENGTH: 15
<212> TYPE: PRT
<213> ORGANISM: Canis familiaris

<400> SEQUENCE: 24

Thr Glu Phe Ser His Pro Val Tyr Cys Ala Asn Pro Pro Asp Cys
1               5                   10                  15

<210> SEQ ID NO 25
<211> LENGTH: 15
<212> TYPE: PRT
<213> ORGANISM: Canis familiaris

<400> SEQUENCE: 25

Phe Ser His Pro Val Tyr Cys Ala Asn Pro Pro Asp Cys Leu Ala
1               5                   10                  15

<210> SEQ ID NO 26
<211> LENGTH: 15
<212> TYPE: PRT
<213> ORGANISM: Canis familiaris

<400> SEQUENCE: 26

His Pro Val Tyr Cys Ala Asn Pro Pro Asp Cys Leu Ala Arg Ile
1               5                   10                  15

<210> SEQ ID NO 27
<211> LENGTH: 15
<212> TYPE: PRT
<213> ORGANISM: Canis familiaris

<400> SEQUENCE: 27

Val Tyr Cys Ala Asn Pro Pro Asp Cys Leu Ala Arg Ile Glu Arg
1               5                   10                  15

<210> SEQ ID NO 28
<211> LENGTH: 15
<212> TYPE: PRT
<213> ORGANISM: Canis familiaris

<400> SEQUENCE: 28
```

-continued

```
Cys Ala Asn Pro Pro Asp Cys Leu Ala Arg Ile Glu Arg Leu Thr
1               5                   10                  15

<210> SEQ ID NO 29
<211> LENGTH: 15
<212> TYPE: PRT
<213> ORGANISM: Canis familiaris

<400> SEQUENCE: 29

Asn Pro Pro Asp Cys Leu Ala Arg Ile Glu Arg Leu Thr Leu His
1               5                   10                  15

<210> SEQ ID NO 30
<211> LENGTH: 15
<212> TYPE: PRT
<213> ORGANISM: Canis familiaris

<400> SEQUENCE: 30

Pro Asp Cys Leu Ala Arg Ile Glu Arg Leu Thr Leu His Arg Ile
1               5                   10                  15

<210> SEQ ID NO 31
<211> LENGTH: 15
<212> TYPE: PRT
<213> ORGANISM: Canis familiaris

<400> SEQUENCE: 31

Cys Leu Ala Arg Ile Glu Arg Leu Thr Leu His Arg Ile Arg Gly
1               5                   10                  15

<210> SEQ ID NO 32
<211> LENGTH: 15
<212> TYPE: PRT
<213> ORGANISM: Canis familiaris

<400> SEQUENCE: 32

Ala Arg Ile Glu Arg Leu Thr Leu His Arg Ile Arg Gly Cys Ala
1               5                   10                  15

<210> SEQ ID NO 33
<211> LENGTH: 15
<212> TYPE: PRT
<213> ORGANISM: Canis familiaris

<400> SEQUENCE: 33

Ile Glu Arg Leu Thr Leu His Arg Ile Arg Gly Cys Ala Ser Gly
1               5                   10                  15

<210> SEQ ID NO 34
<211> LENGTH: 15
<212> TYPE: PRT
<213> ORGANISM: Canis familiaris

<400> SEQUENCE: 34

Arg Leu Thr Leu His Arg Ile Arg Gly Cys Ala Ser Gly Ala Arg
1               5                   10                  15

<210> SEQ ID NO 35
<211> LENGTH: 15
<212> TYPE: PRT
<213> ORGANISM: Canis familiaris

<400> SEQUENCE: 35

Thr Leu His Arg Ile Arg Gly Cys Ala Ser Gly Ala Arg Glu Ala
1               5                   10                  15
```

<210> SEQ ID NO 36
<211> LENGTH: 15
<212> TYPE: PRT
<213> ORGANISM: Canis familiaris

<400> SEQUENCE: 36

His Arg Ile Arg Gly Cys Ala Ser Gly Ala Arg Glu Ala Phe Ala
1               5                   10                  15

<210> SEQ ID NO 37
<211> LENGTH: 15
<212> TYPE: PRT
<213> ORGANISM: Canis familiaris

<400> SEQUENCE: 37

Ile Arg Gly Cys Ala Ser Gly Ala Arg Glu Ala Phe Ala Glu Gly
1               5                   10                  15

<210> SEQ ID NO 38
<211> LENGTH: 15
<212> TYPE: PRT
<213> ORGANISM: Canis familiaris

<400> SEQUENCE: 38

Gly Cys Ala Ser Gly Ala Arg Glu Ala Phe Ala Glu Gly Thr Val
1               5                   10                  15

<210> SEQ ID NO 39
<211> LENGTH: 15
<212> TYPE: PRT
<213> ORGANISM: Canis familiaris

<400> SEQUENCE: 39

Ala Ser Gly Ala Arg Glu Ala Phe Ala Glu Gly Thr Val Ala Ala
1               5                   10                  15

<210> SEQ ID NO 40
<211> LENGTH: 15
<212> TYPE: PRT
<213> ORGANISM: Canis familiaris

<400> SEQUENCE: 40

Gly Ala Arg Glu Ala Phe Ala Glu Gly Thr Val Ala Ala Leu Ala
1               5                   10                  15

<210> SEQ ID NO 41
<211> LENGTH: 15
<212> TYPE: PRT
<213> ORGANISM: Canis familiaris

<400> SEQUENCE: 41

Arg Glu Ala Phe Ala Glu Gly Thr Val Ala Ala Leu Ala Ala Glu
1               5                   10                  15

<210> SEQ ID NO 42
<211> LENGTH: 15
<212> TYPE: PRT
<213> ORGANISM: Canis familiaris

<400> SEQUENCE: 42

Ala Phe Ala Glu Gly Thr Val Ala Ala Leu Ala Ala Glu Cys Pro
1               5                   10                  15

```
<210> SEQ ID NO 43
<211> LENGTH: 15
<212> TYPE: PRT
<213> ORGANISM: Canis familiaris

<400> SEQUENCE: 43

Ala Glu Gly Thr Val Ala Ala Leu Ala Ala Glu Cys Pro Gly Tyr
1               5                   10                  15

<210> SEQ ID NO 44
<211> LENGTH: 15
<212> TYPE: PRT
<213> ORGANISM: Canis familiaris

<400> SEQUENCE: 44

Gly Thr Val Ala Ala Leu Ala Ala Glu Cys Pro Gly Tyr Ala Ala
1               5                   10                  15

<210> SEQ ID NO 45
<211> LENGTH: 15
<212> TYPE: PRT
<213> ORGANISM: Canis familiaris

<400> SEQUENCE: 45

Val Ala Ala Leu Ala Ala Glu Cys Pro Gly Tyr Ala Ala Ala Pro
1               5                   10                  15

<210> SEQ ID NO 46
<211> LENGTH: 15
<212> TYPE: PRT
<213> ORGANISM: Canis familiaris

<400> SEQUENCE: 46

Ala Leu Ala Ala Glu Cys Pro Gly Tyr Ala Ala Ala Pro Ile Asn
1               5                   10                  15

<210> SEQ ID NO 47
<211> LENGTH: 15
<212> TYPE: PRT
<213> ORGANISM: Canis familiaris

<400> SEQUENCE: 47

Ala Ala Glu Cys Pro Gly Tyr Ala Ala Ala Pro Ile Asn Asn Thr
1               5                   10                  15

<210> SEQ ID NO 48
<211> LENGTH: 15
<212> TYPE: PRT
<213> ORGANISM: Canis familiaris

<400> SEQUENCE: 48

Glu Cys Pro Gly Tyr Ala Ala Ala Pro Ile Asn Asn Thr Gln Ala
1               5                   10                  15

<210> SEQ ID NO 49
<211> LENGTH: 15
<212> TYPE: PRT
<213> ORGANISM: Canis familiaris

<400> SEQUENCE: 49

Pro Gly Tyr Ala Ala Ala Pro Ile Asn Asn Thr Gln Ala Lys Lys
1               5                   10                  15

<210> SEQ ID NO 50
<211> LENGTH: 15
```

```
<212> TYPE: PRT
<213> ORGANISM: Canis familiaris

<400> SEQUENCE: 50

Tyr Ala Ala Ala Pro Ile Asn Asn Thr Gln Ala Lys Lys Lys Arg
1               5                   10                  15

<210> SEQ ID NO 51
<211> LENGTH: 15
<212> TYPE: PRT
<213> ORGANISM: Canis familiaris

<400> SEQUENCE: 51

Ala Ala Pro Ile Asn Asn Thr Gln Ala Lys Lys Lys Arg Lys Lys
1               5                   10                  15

<210> SEQ ID NO 52
<211> LENGTH: 15
<212> TYPE: PRT
<213> ORGANISM: Canis familiaris

<400> SEQUENCE: 52

Pro Ile Asn Asn Thr Gln Ala Lys Lys Lys Arg Lys Lys Arg Gly
1               5                   10                  15

<210> SEQ ID NO 53
<211> LENGTH: 15
<212> TYPE: PRT
<213> ORGANISM: Canis familiaris

<400> SEQUENCE: 53

Asn Asn Thr Gln Ala Lys Lys Lys Arg Lys Lys Arg Gly Val Thr
1               5                   10                  15

<210> SEQ ID NO 54
<211> LENGTH: 15
<212> TYPE: PRT
<213> ORGANISM: Canis familiaris

<400> SEQUENCE: 54

Thr Gln Ala Lys Lys Lys Arg Lys Lys Arg Gly Val Thr Thr Asn
1               5                   10                  15

<210> SEQ ID NO 55
<211> LENGTH: 15
<212> TYPE: PRT
<213> ORGANISM: Canis familiaris

<400> SEQUENCE: 55

Ala Lys Lys Lys Arg Lys Lys Arg Gly Val Thr Thr Asn Lys Cys
1               5                   10                  15

<210> SEQ ID NO 56
<211> LENGTH: 15
<212> TYPE: PRT
<213> ORGANISM: Canis familiaris

<400> SEQUENCE: 56

Lys Lys Arg Lys Lys Arg Gly Val Thr Thr Asn Lys Cys Arg Glu
1               5                   10                  15

<210> SEQ ID NO 57
<211> LENGTH: 15
<212> TYPE: PRT
<213> ORGANISM: Canis familiaris
```

<400> SEQUENCE: 57

Arg Lys Lys Arg Gly Val Thr Thr Asn Lys Cys Arg Glu Gln Val
1               5                   10                  15

<210> SEQ ID NO 58
<211> LENGTH: 15
<212> TYPE: PRT
<213> ORGANISM: Canis familiaris

<400> SEQUENCE: 58

Lys Arg Gly Val Thr Thr Asn Lys Cys Arg Glu Gln Val Ala His
1               5                   10                  15

<210> SEQ ID NO 59
<211> LENGTH: 15
<212> TYPE: PRT
<213> ORGANISM: Canis familiaris

<400> SEQUENCE: 59

Gly Val Thr Thr Asn Lys Cys Arg Glu Gln Val Ala His Leu Ile
1               5                   10                  15

<210> SEQ ID NO 60
<211> LENGTH: 15
<212> TYPE: PRT
<213> ORGANISM: Canis familiaris

<400> SEQUENCE: 60

Thr Thr Asn Lys Cys Arg Glu Gln Val Ala His Leu Ile Gly Leu
1               5                   10                  15

<210> SEQ ID NO 61
<211> LENGTH: 15
<212> TYPE: PRT
<213> ORGANISM: Canis familiaris

<400> SEQUENCE: 61

Asn Lys Cys Arg Glu Gln Val Ala His Leu Ile Gly Leu Trp Arg
1               5                   10                  15

<210> SEQ ID NO 62
<211> LENGTH: 15
<212> TYPE: PRT
<213> ORGANISM: Canis familiaris

<400> SEQUENCE: 62

Cys Arg Glu Gln Val Ala His Leu Ile Gly Leu Trp Arg Arg Phe
1               5                   10                  15

<210> SEQ ID NO 63
<211> LENGTH: 15
<212> TYPE: PRT
<213> ORGANISM: Canis familiaris

<400> SEQUENCE: 63

Glu Gln Val Ala His Leu Ile Gly Leu Trp Arg Arg Phe Ser Arg
1               5                   10                  15

<210> SEQ ID NO 64
<211> LENGTH: 15
<212> TYPE: PRT
<213> ORGANISM: Canis familiaris

<400> SEQUENCE: 64

```
Val Ala His Leu Ile Gly Leu Trp Arg Arg Phe Ser Arg Ile Ser
1               5                   10                  15
```

<210> SEQ ID NO 65
<211> LENGTH: 15
<212> TYPE: PRT
<213> ORGANISM: Canis familiaris

<400> SEQUENCE: 65

```
Tyr Asn Phe Ile Asp Cys Asp Phe Glu Lys Ile Arg Trp Lys Tyr
1               5                   10                  15
```

<210> SEQ ID NO 66
<211> LENGTH: 15
<212> TYPE: PRT
<213> ORGANISM: Canis familiaris

<400> SEQUENCE: 66

```
Phe Ile Asp Cys Asp Phe Glu Lys Ile Arg Trp Lys Tyr Gln Glu
1               5                   10                  15
```

<210> SEQ ID NO 67
<211> LENGTH: 15
<212> TYPE: PRT
<213> ORGANISM: Canis familiaris

<400> SEQUENCE: 67

```
Asp Cys Asp Phe Glu Lys Ile Arg Trp Lys Tyr Gln Glu Val Ile
1               5                   10                  15
```

<210> SEQ ID NO 68
<211> LENGTH: 15
<212> TYPE: PRT
<213> ORGANISM: Canis familiaris

<400> SEQUENCE: 68

```
Asp Phe Glu Lys Ile Arg Trp Lys Tyr Gln Glu Val Ile Tyr Gln
1               5                   10                  15
```

<210> SEQ ID NO 69
<211> LENGTH: 15
<212> TYPE: PRT
<213> ORGANISM: Canis familiaris

<400> SEQUENCE: 69

```
Glu Lys Ile Arg Trp Lys Tyr Gln Glu Val Ile Tyr Gln Ala Leu
1               5                   10                  15
```

<210> SEQ ID NO 70
<211> LENGTH: 15
<212> TYPE: PRT
<213> ORGANISM: Canis familiaris

<400> SEQUENCE: 70

```
Ile Arg Trp Lys Tyr Gln Glu Val Ile Tyr Gln Ala Leu Glu Lys
1               5                   10                  15
```

<210> SEQ ID NO 71
<211> LENGTH: 15
<212> TYPE: PRT
<213> ORGANISM: Canis familiaris

<400> SEQUENCE: 71

Trp Lys Tyr Gln Glu Val Ile Tyr Gln Ala Leu Glu Lys Tyr Met

```
1               5                  10                  15
```

<210> SEQ ID NO 72
<211> LENGTH: 15
<212> TYPE: PRT
<213> ORGANISM: Canis familiaris

<400> SEQUENCE: 72

```
Tyr Gln Glu Val Ile Tyr Gln Ala Leu Glu Lys Tyr Met Asp Gly
1               5                  10                  15
```

<210> SEQ ID NO 73
<211> LENGTH: 15
<212> TYPE: PRT
<213> ORGANISM: Canis familiaris

<400> SEQUENCE: 73

```
Glu Val Ile Tyr Gln Ala Leu Glu Lys Tyr Met Asp Gly Thr Arg
1               5                  10                  15
```

<210> SEQ ID NO 74
<211> LENGTH: 15
<212> TYPE: PRT
<213> ORGANISM: Canis familiaris

<400> SEQUENCE: 74

```
Ile Tyr Gln Ala Leu Glu Lys Tyr Met Asp Gly Thr Arg Ser Thr
1               5                  10                  15
```

<210> SEQ ID NO 75
<211> LENGTH: 15
<212> TYPE: PRT
<213> ORGANISM: Canis familiaris

<400> SEQUENCE: 75

```
Gln Ala Leu Glu Lys Tyr Met Asp Gly Thr Arg Ser Thr Glu Phe
1               5                  10                  15
```

<210> SEQ ID NO 76
<211> LENGTH: 15
<212> TYPE: PRT
<213> ORGANISM: Canis familiaris

<400> SEQUENCE: 76

```
Leu Glu Lys Tyr Met Asp Gly Thr Arg Ser Thr Glu Phe Ser His
1               5                  10                  15
```

<210> SEQ ID NO 77
<211> LENGTH: 15
<212> TYPE: PRT
<213> ORGANISM: Canis familiaris

<400> SEQUENCE: 77

```
Lys Tyr Met Asp Gly Thr Arg Ser Thr Glu Phe Ser His Pro Val
1               5                  10                  15
```

<210> SEQ ID NO 78
<211> LENGTH: 15
<212> TYPE: PRT
<213> ORGANISM: Canis familiaris

<400> SEQUENCE: 78

```
Met Asp Gly Thr Arg Ser Thr Glu Phe Ser His Pro Val Tyr Cys
1               5                  10                  15
```

```
<210> SEQ ID NO 79
<211> LENGTH: 15
<212> TYPE: PRT
<213> ORGANISM: Canis familiaris

<400> SEQUENCE: 79

Gly Thr Arg Ser Thr Glu Phe Ser His Pro Val Tyr Cys Ala Asn
1               5                   10                  15

<210> SEQ ID NO 80
<211> LENGTH: 15
<212> TYPE: PRT
<213> ORGANISM: Canis familiaris

<400> SEQUENCE: 80

Arg Ser Thr Glu Phe Ser His Pro Val Tyr Cys Ala Asn Pro Pro
1               5                   10                  15

<210> SEQ ID NO 81
<211> LENGTH: 15
<212> TYPE: PRT
<213> ORGANISM: Canis familiaris

<400> SEQUENCE: 81

Thr Glu Phe Ser His Pro Val Tyr Cys Ala Asn Pro Pro Asp Cys
1               5                   10                  15

<210> SEQ ID NO 82
<211> LENGTH: 15
<212> TYPE: PRT
<213> ORGANISM: Canis familiaris

<400> SEQUENCE: 82

Phe Ser His Pro Val Tyr Cys Ala Asn Pro Pro Asp Cys Leu Ala
1               5                   10                  15

<210> SEQ ID NO 83
<211> LENGTH: 15
<212> TYPE: PRT
<213> ORGANISM: Canis familiaris

<400> SEQUENCE: 83

His Pro Val Tyr Cys Ala Asn Pro Pro Asp Cys Leu Ala Arg Ile
1               5                   10                  15

<210> SEQ ID NO 84
<211> LENGTH: 15
<212> TYPE: PRT
<213> ORGANISM: Canis familiaris

<400> SEQUENCE: 84

Val Tyr Cys Ala Asn Pro Pro Asp Cys Leu Ala Arg Ile Glu Arg
1               5                   10                  15

<210> SEQ ID NO 85
<211> LENGTH: 15
<212> TYPE: PRT
<213> ORGANISM: Canis familiaris

<400> SEQUENCE: 85

Cys Ala Asn Pro Pro Asp Cys Leu Ala Arg Ile Glu Arg Leu Thr
1               5                   10                  15

<210> SEQ ID NO 86
```

```
<211> LENGTH: 15
<212> TYPE: PRT
<213> ORGANISM: Canis familiaris

<400> SEQUENCE: 86

Asn Pro Pro Asp Cys Leu Ala Arg Ile Glu Arg Leu Thr Leu His
1               5                   10                  15

<210> SEQ ID NO 87
<211> LENGTH: 15
<212> TYPE: PRT
<213> ORGANISM: Canis familiaris

<400> SEQUENCE: 87

Pro Asp Cys Leu Ala Arg Ile Glu Arg Leu Thr Leu His Arg Ile
1               5                   10                  15

<210> SEQ ID NO 88
<211> LENGTH: 15
<212> TYPE: PRT
<213> ORGANISM: Canis familiaris

<400> SEQUENCE: 88

Cys Leu Ala Arg Ile Glu Arg Leu Thr Leu His Arg Ile Arg Gly
1               5                   10                  15

<210> SEQ ID NO 89
<211> LENGTH: 15
<212> TYPE: PRT
<213> ORGANISM: Canis familiaris

<400> SEQUENCE: 89

Ala Arg Ile Glu Arg Leu Thr Leu His Arg Ile Arg Gly Cys Ala
1               5                   10                  15

<210> SEQ ID NO 90
<211> LENGTH: 15
<212> TYPE: PRT
<213> ORGANISM: Canis familiaris

<400> SEQUENCE: 90

Ile Glu Arg Leu Thr Leu His Arg Ile Arg Gly Cys Ala Ser Gly
1               5                   10                  15

<210> SEQ ID NO 91
<211> LENGTH: 15
<212> TYPE: PRT
<213> ORGANISM: Canis familiaris

<400> SEQUENCE: 91

Arg Leu Thr Leu His Arg Ile Arg Gly Cys Ala Ser Gly Ala Arg
1               5                   10                  15

<210> SEQ ID NO 92
<211> LENGTH: 15
<212> TYPE: PRT
<213> ORGANISM: Canis familiaris

<400> SEQUENCE: 92

Thr Leu His Arg Ile Arg Gly Cys Ala Ser Gly Ala Arg Glu Ala
1               5                   10                  15

<210> SEQ ID NO 93
<211> LENGTH: 15
<212> TYPE: PRT
```

<213> ORGANISM: Canis familiaris

<400> SEQUENCE: 93

```
His Arg Ile Arg Gly Cys Ala Ser Gly Ala Arg Glu Ala Phe Ala
1               5                   10                  15
```

<210> SEQ ID NO 94
<211> LENGTH: 15
<212> TYPE: PRT
<213> ORGANISM: Canis familiaris

<400> SEQUENCE: 94

```
Ile Arg Gly Cys Ala Ser Gly Ala Arg Glu Ala Phe Ala Glu Gly
1               5                   10                  15
```

<210> SEQ ID NO 95
<211> LENGTH: 15
<212> TYPE: PRT
<213> ORGANISM: Canis familiaris

<400> SEQUENCE: 95

```
Gly Cys Ala Ser Gly Ala Arg Glu Ala Phe Ala Glu Gly Thr Val
1               5                   10                  15
```

<210> SEQ ID NO 96
<211> LENGTH: 15
<212> TYPE: PRT
<213> ORGANISM: Canis familiaris

<400> SEQUENCE: 96

```
Ala Ser Gly Ala Arg Glu Ala Phe Ala Glu Gly Thr Val Ala Ala
1               5                   10                  15
```

<210> SEQ ID NO 97
<211> LENGTH: 15
<212> TYPE: PRT
<213> ORGANISM: Canis familiaris

<400> SEQUENCE: 97

```
Gly Ala Arg Glu Ala Phe Ala Glu Gly Thr Val Ala Ala Leu Ala
1               5                   10                  15
```

<210> SEQ ID NO 98
<211> LENGTH: 15
<212> TYPE: PRT
<213> ORGANISM: Canis familiaris

<400> SEQUENCE: 98

```
Arg Glu Ala Phe Ala Glu Gly Thr Val Ala Ala Leu Ala Ala Glu
1               5                   10                  15
```

<210> SEQ ID NO 99
<211> LENGTH: 15
<212> TYPE: PRT
<213> ORGANISM: Canis familiaris

<400> SEQUENCE: 99

```
Ala Phe Ala Glu Gly Thr Val Ala Ala Leu Ala Ala Glu Cys Pro
1               5                   10                  15
```

<210> SEQ ID NO 100
<211> LENGTH: 15
<212> TYPE: PRT
<213> ORGANISM: Canis familiaris

```
<400> SEQUENCE: 100

Ala Glu Gly Thr Val Ala Ala Leu Ala Ala Glu Cys Pro Gly Tyr
1               5                   10                  15

<210> SEQ ID NO 101
<211> LENGTH: 15
<212> TYPE: PRT
<213> ORGANISM: Canis familiaris

<400> SEQUENCE: 101

Gly Thr Val Ala Ala Leu Ala Ala Glu Cys Pro Gly Tyr Ala Ala
1               5                   10                  15

<210> SEQ ID NO 102
<211> LENGTH: 57
<212> TYPE: PRT
<213> ORGANISM: Homo sapiens

<400> SEQUENCE: 102

Leu Tyr Val Leu Ser Val Ser Phe Arg Lys Ile Phe Ile Leu Gln Leu
1               5                   10                  15

Val Gly Leu Val Leu Thr Tyr Asp Phe Thr Asn Cys Asp Phe Glu Lys
            20                  25                  30

Ile Lys Ala Ala Tyr Leu Ser Thr Ile Ser Lys Asp Leu Ile Thr Tyr
        35                  40                  45

Met Ser Gly Thr Lys Ser Thr Glu Phe
    50                  55

<210> SEQ ID NO 103
<211> LENGTH: 55
<212> TYPE: PRT
<213> ORGANISM: Canis familiaris

<400> SEQUENCE: 103

Leu Ile Ile Cys Ser Val Ser Val Phe Arg Lys Ile Phe Val Leu Gln
1               5                   10                  15

Leu Val Gly Leu Val Leu Thr Tyr Asn Phe Ile Asp Cys Asp Phe Glu
            20                  25                  30

Lys Ile Arg Trp Lys Tyr Gln Glu Val Ile Tyr Gln Ala Leu Glu Lys
        35                  40                  45

Tyr Met Asp Gly Val Ser Glu
    50                  55

<210> SEQ ID NO 104
<211> LENGTH: 42
<212> TYPE: PRT
<213> ORGANISM: Homo sapiens

<400> SEQUENCE: 104

Gln Ile Asn Ala Thr Gln Ala Met Lys Lys Arg Arg Lys Arg Lys Val
1               5                   10                  15

Thr Thr Asn Lys Cys Leu Glu Gln Val Ser Gln Leu Gln Gly Leu Trp
            20                  25                  30

Arg Arg Phe Asn Arg Pro Leu Leu Lys Gln
        35                  40

<210> SEQ ID NO 105
<211> LENGTH: 39
<212> TYPE: PRT
<213> ORGANISM: Canis familiaris
```

<400> SEQUENCE: 105

Gln Ile Asn Asn Thr Gln Ala Lys Lys Arg Lys Lys Arg Gly Val
1               5                   10                  15

Thr Thr Asn Lys Cys Arg Glu Gln Val Ala His Leu Ile Gly Leu Trp
            20                  25                  30

Arg Arg Phe Ser Arg Ile Ser
            35

<210> SEQ ID NO 106
<211> LENGTH: 44
<212> TYPE: PRT
<213> ORGANISM: Homo sapiens

<400> SEQUENCE: 106

Leu Thr Glu Ile Gln Ser Leu Thr Phe Asn Pro Thr Ala Gly Cys Ala
1               5                   10                  15

Ser Leu Ala Lys Glu Met Phe Ala Met Lys Thr Lys Ala Ala Leu Ala
            20                  25                  30

Ile Trp Cys Pro Gly Tyr Ser Glu Thr Gln Ile Asn
        35                  40

<210> SEQ ID NO 107
<211> LENGTH: 44
<212> TYPE: PRT
<213> ORGANISM: Canis familiaris

<400> SEQUENCE: 107

Leu Ala Arg Ile Glu Arg Leu Thr Leu His Arg Ile Arg Gly Cys Ala
1               5                   10                  15

Ser Gly Ala Arg Glu Ala Phe Ala Glu Gly Thr Val Ala Ala Leu Ala
            20                  25                  30

Ala Glu Cys Pro Gly Tyr Ala Ala Ala Pro Val Ser
        35                  40

<210> SEQ ID NO 108
<211> LENGTH: 32
<212> TYPE: PRT
<213> ORGANISM: Homo sapiens

<400> SEQUENCE: 108

Thr Ala Gly Cys Ala Ser Leu Ala Lys Glu Met Phe Ala Met Lys Thr
1               5                   10                  15

Lys Ala Ala Leu Ala Ile Trp Cys Pro Gly Tyr Ser Glu Thr Gln Ile
            20                  25                  30

<210> SEQ ID NO 109
<211> LENGTH: 32
<212> TYPE: PRT
<213> ORGANISM: Canis familiaris

<400> SEQUENCE: 109

Thr Pro Gly Cys Gly Ile Cys Ala Lys Glu Ala Ala Ala Leu Gly Trp
1               5                   10                  15

Phe Cys Ala Leu Ser Val Trp Cys Pro Gly Trp Ala Gln Thr Gln Val
            20                  25                  30

<210> SEQ ID NO 110
<211> LENGTH: 44
<212> TYPE: PRT
<213> ORGANISM: Homo sapiens

```
<400> SEQUENCE: 110

Leu Thr Glu Ile Gln Ser Leu Thr Phe Asn Pro Thr Ala Gly Cys Ala
1               5                   10                  15

Ser Leu Ala Lys Glu Met Phe Ala Met Lys Thr Lys Ala Ala Leu Ala
            20                  25                  30

Ile Trp Cys Pro Gly Tyr Ser Glu Thr Gln Ile Asn
        35                  40

<210> SEQ ID NO 111
<211> LENGTH: 44
<212> TYPE: PRT
<213> ORGANISM: Canis familiaris

<400> SEQUENCE: 111

Leu Ala Arg Ile Glu Arg Leu Thr Leu His Arg Ile Arg Gly Cys Ala
1               5                   10                  15

Ser Gly Ala Arg Glu Ala Phe Ala Glu Gly Thr Val Ala Ala Leu Ala
            20                  25                  30

Ala Glu Cys Pro Gly Tyr Ala Ala Ala Pro Val Ser
        35                  40

<210> SEQ ID NO 112
<211> LENGTH: 32
<212> TYPE: PRT
<213> ORGANISM: Homo sapiens

<400> SEQUENCE: 112

Thr Ala Gly Cys Ala Ser Leu Ala Lys Glu Met Phe Ala Met Lys Thr
1               5                   10                  15

Lys Ala Ala Leu Ala Ile Trp Cys Pro Gly Tyr Ser Glu Thr Gln Ile
            20                  25                  30

<210> SEQ ID NO 113
<211> LENGTH: 32
<212> TYPE: PRT
<213> ORGANISM: Canis familiaris

<400> SEQUENCE: 113

Thr Pro Gly Cys Gly Ile Cys Ala Lys Glu Ala Ala Ala Leu Gly Trp
1               5                   10                  15

Phe Cys Ala Leu Ser Val Trp Cys Pro Gly Trp Ala Gln Thr Gln Val
            20                  25                  30

<210> SEQ ID NO 114
<211> LENGTH: 139
<212> TYPE: PRT
<213> ORGANISM: Canis familiaris

<400> SEQUENCE: 114

Arg Lys Ile Phe Val Leu Gln Leu Val Gly Leu Val Leu Thr Tyr Asn
1               5                   10                  15

Phe Ile Asp Cys Asp Phe Glu Lys Ile Arg Trp Lys Tyr Gln Glu Val
            20                  25                  30

Ile Tyr Gln Ala Leu Glu Lys Tyr Met Asp Gly Thr Arg Ser Thr Glu
        35                  40                  45

Phe Ser His Pro Val Tyr Cys Ala Asn Pro Pro Asp Cys Leu Ala Arg
    50                  55                  60

Ile Glu Arg Leu Thr Leu His Arg Ile Arg Gly Cys Ala Ser Gly Ala
65                  70                  75                  80
```

-continued

Arg Glu Ala Phe Ala Glu Gly Thr Val Ala Ala Leu Ala Ala Glu Cys
                85                  90                  95

Pro Gly Tyr Ala Ala Ala Pro Ile Asn Asn Thr Gln Ala Lys Lys Lys
            100                 105                 110

Arg Lys Lys Arg Gly Val Thr Thr Asn Lys Cys Arg Glu Gln Val Ala
        115                 120                 125

His Leu Ile Gly Leu Trp Arg Arg Phe Ser Arg
    130                 135

<210> SEQ ID NO 115
<211> LENGTH: 139
<212> TYPE: PRT
<213> ORGANISM: Homo sapiens

<400> SEQUENCE: 115

Arg Lys Ile Phe Ile Leu Gln Leu Val Gly Leu Val Leu Thr Tyr Asp
1               5                   10                  15

Phe Thr Asn Cys Asp Phe Glu Lys Ile Lys Ala Ala Tyr Leu Ser Thr
            20                  25                  30

Ile Ser Lys Asp Leu Ile Thr Tyr Met Ser Gly Thr Lys Ser Thr Glu
        35                  40                  45

Phe Asn Asn Thr Val Ser Cys Ser Asn Arg Pro His Cys Leu Thr Glu
    50                  55                  60

Ile Gln Ser Leu Thr Phe Asn Pro Thr Ala Gly Cys Ala Ser Leu Ala
65                  70                  75                  80

Lys Glu Met Phe Ala Met Lys Thr Lys Ala Ala Leu Ala Ile Trp Cys
                85                  90                  95

Pro Gly Tyr Ser Glu Thr Gln Ile Asn Ala Thr Gln Ala Met Lys Lys
            100                 105                 110

Arg Arg Lys Arg Lys Val Thr Thr Asn Lys Cys Leu Glu Gln Val Ser
        115                 120                 125

Gln Leu Gln Gly Leu Trp Arg Arg Phe Asn Arg
    130                 135

<210> SEQ ID NO 116
<211> LENGTH: 137
<212> TYPE: PRT
<213> ORGANISM: Canis familiaris

<400> SEQUENCE: 116

Arg Lys Ile Phe Val Leu Gln Leu Val Gly Leu Val Leu Thr Tyr Asn
1               5                   10                  15

Phe Ile Asp Cys Asp Phe Glu Lys Ile Arg Trp Lys Tyr Gln Glu Val
            20                  25                  30

Ile Tyr Gln Ala Leu Glu Lys Tyr Met Asp Gly Thr Arg Ser Thr Glu
        35                  40                  45

Phe Ser His Pro Val Tyr Cys Ala Asn Pro Pro Asp Cys Leu Ala Arg
    50                  55                  60

Ile Glu Arg Leu Thr Leu His Arg Ile Arg Gly Cys Ala Ser Gly Ala
65                  70                  75                  80

Arg Glu Ala Phe Ala Glu Gly Thr Val Ala Ala Leu Ala Ala Glu Cys
                85                  90                  95

Pro Gly Tyr Ala Ala Ala Pro Ile Asn Asn Thr Gln Ala Lys Lys Lys
            100                 105                 110

Arg Lys Lys Arg Gly Val Thr Thr Asn Lys Cys Arg Glu Gln Val Ala
        115                 120                 125

-continued

```
His Leu Ile Gly Leu Trp Arg Arg Phe
    130                 135

<210> SEQ ID NO 117
<211> LENGTH: 131
<212> TYPE: PRT
<213> ORGANISM: Mus sp.

<400> SEQUENCE: 117

Arg Ser Leu Phe Ile Leu Gln Val Leu Val Arg Met Gly Leu Thr Tyr
1               5                   10                  15

Asn Phe Ser Asn Cys Asn Phe Thr Ser Ile Thr Lys Ile Tyr Cys Asn
            20                  25                  30

Ile Ile Phe His Asp Leu Thr Gly Asp Leu Lys Gly Ala Lys Phe Glu
                35                  40                  45

Gln Ile Glu Asp Cys Glu Ser Lys Pro Ala Cys Leu Leu Lys Ile Glu
        50                  55                  60

Tyr Tyr Thr Leu Asn Pro Ile Pro Gly Cys Pro Ser Leu Pro Asp Lys
65                  70                  75                  80

Thr Phe Ala Arg Arg Thr Arg Glu Ala Leu Asn Asp His Cys Pro Gly
                85                  90                  95

Tyr Pro Glu Thr Glu Arg Asn Asp Gly Thr Gln Glu Met Ala Gln Glu
            100                 105                 110

Val Gln Asn Ile Cys Leu Asn Gln Thr Ser Gln Ile Leu Arg Leu Trp
        115                 120                 125

Tyr Ser Phe
    130

<210> SEQ ID NO 118
<211> LENGTH: 22
<212> TYPE: PRT
<213> ORGANISM: Canis familiaris

<400> SEQUENCE: 118

Asn Pro Pro Asp Cys Leu Ala Arg Ile Glu Arg Leu Thr Leu His Arg
1               5                   10                  15

Ile Arg Gly Cys Ala Ser
            20
```

CANINE THYMIC STROMAL LYMPHOPOIETIN PROTEIN AND USES THEREOF

CROSS-REFERENCE TO RELATED APPLICATIONS

This application is a non-provisional application that claims priority under 35 U.S.C. § 119(e) of provisional application U.S. Ser. No. 60/875,135 filed Dec. 14, 2006, the contents of which are hereby incorporated by reference in its entirety.

FIELD OF THE INVENTION

The present invention relates to canine thymic stromal lymphopoietin protein (canine "TSLP"), nucleic acid molecules, vectors and host cells encoding canine TSLP, and methods of making and using canine TSLP.

BACKGROUND OF THE INVENTION

Animals, including humans, that suffer from reagin-mediated disorders, such as atopic diseases, have a hereditary tendency to develop immediate allergic reactions involving IgE antibodies. Multiple genetic factors contribute to the expression of the resulting phenotype seen in such animals. The immediate hypersensitivity observed in atopic diseases results from exposure to specific allergens, such as the house dust mite (*Dermatophagoides pteronyssinus*), pollens, molds, and danders. Not surprisingly, individuals having an atopic disease are more likely to suffer from asthma, atopic dermatitis, as well as other disorders related to endogenous IgE release.

Atopic diseases such as allergic dermatitis, asthma, and the like, also occur in the canine species, including in domestic dogs. Such dogs generally begin to show signs of atopy between one and three years of age. Due to the hereditary nature of the disease, several breeds, including golden retrievers, most terriers, Irish sellers, Lhasa apsos, Dalmatians, bulldogs and Old English sheep dogs have a greater tendency to be atopic, though other types of dogs, including mixed breeds, also are known to suffer from this condition. The incidence of at least one particular type of atopy, atopic dermatitis, is increasing significantly in both humans and canines alike.

Atopic canines will usually rub, lick, chew, bite or scratch at their feet, muzzle, ears, armpits or groin area, resulting in hair loss, reddening, and thickening of the skin. In some cases several skin conditions combine to cause an animal to itch when a single allergy alone would not have resulted in such itching. These aggravating problems can be due to air borne-allergens (pollens, etc.), allergens in food, and allergens from parasites (fleas, etc.). Bacterial and/or yeast infections of the skin also can augment the itching sensation.

One simple means of alleviating the annoying symptoms of atopy is to avoid the inciting allergen(s). Unfortunately, such avoidance is generally impractical. Heretofore, veterinary practitioners have treated canine atopic dermatitis by administering oral antihistamines, oral or topical corticosteroid anti-inflammatory agents, other immune system suppressants, such as cyclosporine or tacrolimus, fatty acid supplements, and allergen specific immunotherapy (which requires injection of the identified antigen). However, none of these treatments work in all cases. Moreover, such treatments are costly and/or give rise to significant side effects. Thus, there is a longstanding need for safer, more effective and more economical approaches to treating or suppressing the symptoms of canine atopic dermatitis.

The mammalian immune response is based on a series of complex cellular interactions, called the "immune network". Much of the immune response revolves around the network-like interactions of lymphocytes, macrophages, granulocytes, and other cells, with soluble proteins called cytokines playing a critical role in mediating/controlling/regulating these cellular interactions. Thus, cytokines and immune cells serve to mediate specific physiological mechanisms or pathways leading to the various inflammatory disorders.

Allergic inflammation is the result of a complex immunological cascade which leads T cells to produce dysregulated TH2-derived cytokines such as IL-4, IL-5, and IL-13. These cytokines, in turn, trigger bronchial hyperreactivity, IgE production, eosinophilia, and mucus production (see, e.g., Busse and Lemanske, Jr. (2001) *N. Engl. J. Med.* 344:350-62; Holgate (2000) *Br. Med. J.* 320:231-234; and Renauld (2001) *J. Clin. Pathol.* 54:577-589).

Thymic Stromal Lymphopoietin protein (TSLP) is an IL-7-like cytokine that was initially identified in mice as a factor that supported: (i) the in vitro development of surface IgM$^+$ B cells, and (ii) B and T cell proliferation (Friend et al., 1994 Exp Hematology 22:321-328, see also, Levin et al., 1999, J. Immunol 162: 677-683), TSLP is now known to bind a cellular receptor comprising IL-7R-alpha subunit and a unique receptor subunit called TSLP-R. This interaction triggers signal transduction via STAT activation or Thymus and Activation-Regulated Chemokine (TARC) expression in a hematopoietic cell, such as a myeloid lineage cell such as a monocyte, or a dendritic cell. (see, e.g., co-owned U.S. Pat. No. 6,890,734, incorporated herein by reference).

TSLP also may play a significant role in mice in the pathogenesis of allergic diseases such as atopic dermatitis and asthma. For example, transgenic mice in which the expression of TSLP gene was specifically induced in the skin show immunological and clinical features of atopic dermatitis such as eczematous lesions containing inflammatory dermal cellular infiltrates, a dramatic increase in Th$_2$ CD4$^+$ T cells expressing skin homing receptors, and elevated serum levels of IgE. Moreover, lungs of mice expressing a lung-specific TSLP transgene show immunological and clinical features of asthma including massive infiltration of leukocytes, goblet cell hyperplasia, sub-epithelial fibrosis, an increase in T helper type 2 cytokines, and increased levels of IgE.

Sims et al. obtained the cDNA sequence of murine TSLP employing expression cloning, but were unable to clone the human homologue with hybridization probes based on the murine TSLP (Sims et al. 2000, *J exp Med*, 192: 671-680). Subsequently, the human homologue was identified through detailed EST analysis. The human TSLP nucleotide sequence was found to have only 43% homology with the corresponding mouse sequence.

Therefore, there remains a need to provide new and more practical treatments for atopic disorders in canines, including atopic dermatitis and its associated clinical manifestations. Moreover, there is a need to isolate factors that are involved in the immunological cascade that leads to atopic disorders in canines that could lead to the development of such treatments.

The citation of any reference herein should not be construed as an admission that such reference is available as "prior art" to the instant application.

SUMMARY OF THE INVENTION

The present invention provides new and more practical treatments for atopic disorders in canines, including atopic dermatitis and its associated clinical manifestations. Accordingly, the present invention provides novel isolated and/or recombinant thymic stromal lymphopoietin protein (TSLP) proteins that are involved in the immunological cascade that leads to atopic disorders. The present invention further provides antigenic fragments of such TSLP proteins. In a particular aspect of the present invention, the TSLP protein is a canine TSLP protein.

Therefore the present invention provides a TSLP protein comprising an amino acid sequence that has 80% or greater identity to the amino acid sequence of SEQ ID NO: 2, excluding the 28 amino acid residue signal sequence, which when the protein is administered to a canine subject as a vaccine, antibodies that bind the canine TSLP protein comprising the amino acid sequence of SEQ ID NO: 2 are detectable in the resulting canine sera obtained from the vaccinated canine subject. In a related embodiment, the TSLP protein comprises an amino acid sequence that has 80% or greater identity to the amino acid sequence of SEQ ID NO: 2, excluding the 28 amino acid residue signal sequence; and is cross reactive with an antibody raised against the canine TSLP comprising the amino acid of SEQ ID NO: 2.

The present invention further provides a TSLP protein comprising an amino acid sequence that has 80% or greater identity to the amino acid sequence of SEQ ID NO. 2 (excluding the 28 amino acid residue signal sequence) which binds to an epitope-specific canine TSLP monoclonal antibody.

In a more particular embodiment, that TSLP protein comprises an amino acid sequence that has 90% or greater identity to the amino acid sequence of SEQ ID NO: 2, excluding the 28 amino acid residue signal sequence. In still another embodiment, that TSLP protein comprises an amino acid sequence that has 95% or greater identity to the amino acid sequence of SEQ ID NO: 2, excluding the 28 amino acid residue signal sequence.

In a specific embodiment of the present invention, the TSLP protein is the canine TSLP protein that comprises the amino acid sequence of SEQ ID NO: 2. In another embodiment, the TSLP protein is the mature canine TSLP protein that comprises amino acid resides 29-155 of SEQ ID NO: 2.

Antigenic fragments of the TSLP proteins of the present invention are also provided. Such antigenic fragments include those that comprise one or more epitopes individually defined by the amino acid sequences of SEQ ID NOs: 8-101. In a particular embodiment, an antigenic fragment of the present invention comprises one or more epitopes that comprise an amino acid sequence of SEQ ID NOs: 30, 31, 32, and/or 34. In another embodiment, the antigenic fragments can have an amino acid sequence contained within the overlap of the amino acid sequences of SEQ ID NOs: 30, 31, 32, and/or 34, i.e., NPPDCLARIERLTLHRIRGCAS (SEQ ID NO: 118). In a particular embodiment, an antigenic fragment of the canine TSLP protein is capable of binding an anti-human TSLP monoclonal antibody. Antigenic fragments of the amino acid sequence of NPPDCLARIERLTLHRIRGCAS (SEQ ID NO: 118) can range in size from about 5 to about 21 amino acid residues.

Vaccines are also provided that can include an effective amount of any TSLP protein of the present invention, one or more antigenic fragments thereof, or combinations of such full-length protein(s) and one or more of such fragments. In one embodiment the TSLP protein is a canine TSLP protein that comprises the amino acid sequence of SEQ ID NO: 2. In a particular embodiment, a vaccine contains one or more antigenic fragments of the canine TSLP protein that comprises 5 to 22 contiguous amino acids of amino acid residues 71-92 of SEQ ID NO: 2 (identified herein as SEQ ID NO: 118). Examples of such antigenic fragments include the epitopes disclosed herein that comprise amino acid sequences of SEQ ID NO: 30, SEQ ID NO: 31, SEQ ID NO: 32, SEQ ID NO: 33, or SEQ ID NO: 34. All of the vaccines of the present invention can further comprise a pharmaceutically acceptable adjuvant.

A vaccine of the present invention may be employed in a method of inducing anti-canine TSLP antibodies. One such method comprises immunizing a mammal with an effective amount of the vaccine. This method optionally includes a method of downregulating TSLP activity in a canine and/or a method of treating or preventing allergic symptoms in an atopic canine that comprises immunizing the canine with an effective amount of the vaccine. The allergic symptoms ameliorated can include allergic dermatitis, asthma and the like.

A vaccine of the present invention may be administered by a route such as: intramuscular injection, subcutaneous injection, intravenous injection, intradermal injection, oral administration, intranasal administration, scarification, and combinations thereof.

The present invention further provides a nucleic acid molecule encoding a TSLP protein of the present invention or an antigenic fragment thereof. In one such embodiment, the nucleic acid molecule encodes the amino acid sequence of SEQ ID NO: 2. In a particular embodiment of this type, the nucleic acid molecule comprises the nucleotide sequence of SEQ ID NO: 1. Fragments of the nucleotide sequence of SEQ ID NO:1 of about 18 contiguous nucleotides, about 24 contiguous nucleotides, about 36 contiguous nucleotides, about 45 contiguous nucleotides, about 66 contiguous nucleotides, or greater are also part of the present invention. Nucleic acids of about 18 nucleotides, about 24 nucleotides, about 36 nucleotides, about 45 nucleotides, about 66 nucleotides, or greater, including nucleic acids encoding full-length TSLP proteins, that hybridize to SEQ ID NO:1 under stringent hybridization conditions are also provided by the present invention. All of the nucleic acid molecules and fragments thereof of the present invention may further comprise a heterologous nucleotide sequence.

The present invention also provides an expression vector that includes the previously noted nucleic acid molecules and/or fragments thereof. In addition, the present invention provides host cells that comprise such expression vectors. The host cell is optionally a prokaryote or a eukaryote host cell. In one embodiment, the prokaryote host cell is an *Escherichia coli*. In a particular embodiment of this type, the host cell is *E. coli* BL21 (DE3)/pLysS that contains the T7 RNA polymerase gene under the control of the isopropyl-β-D-thiogalactopyranoside (IPTG)-inducible lacUV5 promoter.

The present invention further provides recombinant viral vectors and/or naked DNA vectors comprising one of the above-noted nucleic acid molecules encoding a canine TSLP, e.g., SEQ ID NO: 1, and/or fragment thereof. Such vectors can be used, for example, e.g., in vaccines that are suitable for administration into a canine having atopic dermatitis.

The present invention also provides methods of producing a TSLP protein of the present invention. One such method comprises culturing a host cell of the present invention in a suitable culture medium. This method can further include the step of isolating and/or purifying the TSLP protein from the cultured host cell or the culture medium. The resulting isolated and/or purified TSLP protein is also part of the present invention.

Anti-TSLP antibodies elicited in a hybridoma system by a vaccine of the present invention, are also part of the present invention. In one embodiment of this type a mammalian hybridoma system is employed. In a particular embodiment, the antibodies are isolated and/or purified. The antibodies may be either polyclonol or monoclonal. According to the invention a monoclonal antibody elicited in a non-canine species can be optionally engineered to be caninized, so as to be minimally antigenic when injected into a canine subject. In certain preferred embodiments, the binding domains of any antibody according to the invention is optionally converted into binding fragments smaller than the original antibody, e.g., by cleavage and/or as a recombinant Fv, Fab, and F(ab')$_2$ binding protein. Antibody-derived therapeutic proteins that contain the unique structural and functional properties of naturally-occurring heavy-chain antibodies (e.g., NANOBODIES®) are also included in the invention. In addition, antibody surrogates that have a high affinity for TSLP and low immunogenicity (e.g., avimers prepared from binding portions of the TSLP receptor) are also included in the present invention. The inventive anti-canine TSLP antibodies/avimers can be readily employed in a method of treating allergic symptoms in an atopic canine by administering an effective amount of that anti-canine TSLP antibody.

The present invention also provides a vaccine comprising an effective amount of a non-TSLP immunogen in combination with an effective amount of TSLP protein of the present invention, one or more antigenic fragments thereof or combinations of the full-length protein and one or more of such fragments. In a particular embodiment of this type, the TSLP protein is a canine TSLP protein. In a more particular embodiment, the canine TSLP protein comprises the amino acid sequence of SEQ ID NO:2.

The present invention additionally provides diagnostic methods employing the inventive canine TSLP protein, fragments thereof and/or antibodies elicited by canine TSLP and fragments thereof. In one embodiment, the present invention provides a method of diagnosing atopic dermatitis in a canine comprising obtaining an epidermal sample from the canine and determining the presence of the canine TSLP protein in the epidermal sample.

These and other aspects of the present invention will be better appreciated by reference to the following Figures and the Detailed Description.

BRIEF DESCRIPTION OF THE DRAWINGS

FIG. 7 illustrates a comparison of dog (SEQ ID NO: 32) and the human analog of epitope 25 (SEQ ID NO: 3) TSLP peptide sequence.

FIG. 8A illustrates the DNA Sequence of the canine TSLP gene (SEQ ID NO: 1).

FIG. 8B illustrates the predicted TSLP polypeptide expressed by the DNA sequence illustrated by FIG. 8A (SEQ ID NO: 2). The asterisk marks the N-terminal end of the initial signal sequence (residues 1-28) and the underlined residues 71-92 (SEQ ID NO: 118) represents the domain from which overlapping epitopes 22-26 of Table 2 were determined.

DETAILED DESCRIPTION OF THE INVENTION

Atopic dermatitis ("AD") is a Th2 mediated allergic inflammatory disease. This disease manifests itself with many similar clinical features in human and canine patients. It is likely that the immunopathogenesis of AD in dogs is comparable to AD in humans with respect to cell types and cytokines involved in the skin lesions.

Figure 4:
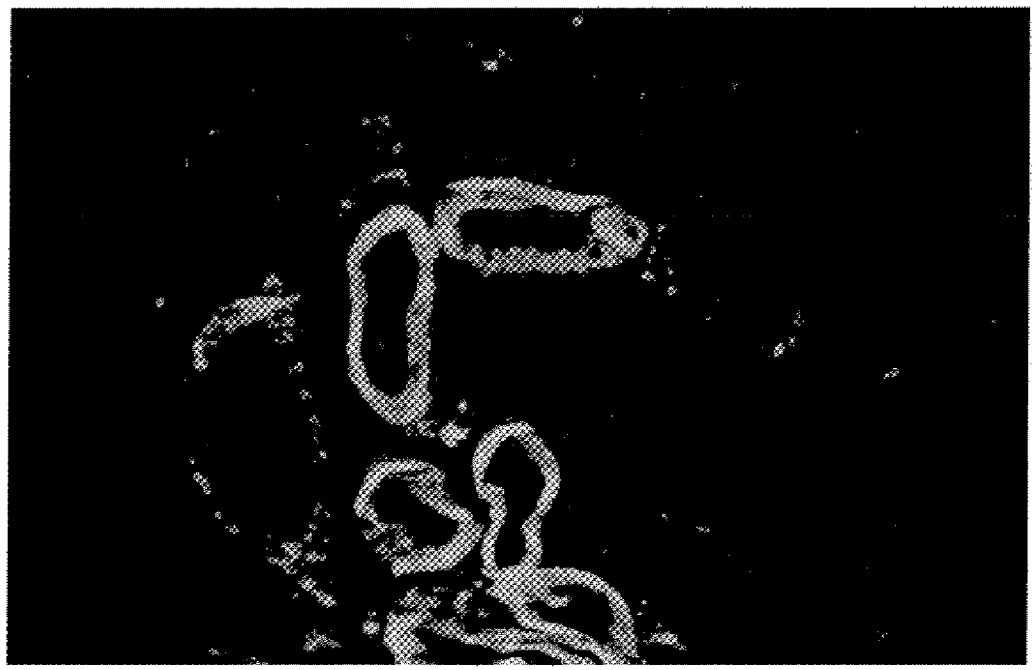
FIG. 4 illustrates FITC staining of a section from a paraffin-embedded block of lesional skin tissue obtained from dog# 10197 that was diagnosed with atopic dermatitis. The section was reacted with rabbit anti-human TSLP polyclonal antibodies and the reaction visualized with Streptavidin-FITC (Fluorescein isothiocyanate). Florescence intensity (light areas) indicates binding of rabbit anti-human TSLP polyclonal antibodies to TSLP present in the tissue.

The binding of the TARC ligand (CCL22) to the CC chemokine receptor 4 (CCR4), which is selectively expressed on Th2 lymphocytes, induces selective migration of these cells to allergic lesions. It has been reported that TARC and its receptor CCR4 are upregulated in lesions of canine AD skin. Since TSLP is a strong inducer of TARC in humans, it was hypothesized that TSLP might be present in the lesions of canine AD. Antibodies raised against human TSLP were therefore tested on lesional skin from AD canine patients. Immunohistochemistry of these skin samples confirmed the presence of antigen reactive with the anti-human TSLP antibody in the lesions, as illustrated by FIG. 4. However, the task of identifying a canine ortholog to the genes encoding murine and human TSLP proved to be particularly difficult due to the high degree of divergence of the nucleic acid and amino acid sequences of TSLP in mammalian species, as disclosed herein.

Immunizing a domestic dog with a TSLP of the present invention and/or one or more antigenic fragments thereof, should serve to reduce endogenous TSLP activity levels and thereby, moderate, eliminate, and/or prevent one or more atopic symptoms, such as those arising in asthma and/or atopic dermatitis, in the immunized dog. In addition, canine TSLP protein can be used as an immunogen for eliciting anti-canine TSLP antibodies for use as a research and/or diagnostic reagent in domestic dogs, or in other mammalian species. Alternatively, in particular instances, the canine TSLP protein and/or nucleic acids that encode the canine TSLP may serve to upregulate elements of the immune system of immune-impaired canines e.g., via STAT activation, or TARC expression, e.g., in hematopoietic cells.

In order to more fully appreciate the instant invention, the following definitions are provided.

The use of singular terms for convenience in description is in no way intended to be so limiting. Thus, for example, reference to a composition comprising "a polypeptide" includes reference to one or more of such polypeptides. As used herein the term "approximately" is used interchangeably with the term "about" and signifies that a value is within twenty percent of the indicated value i.e., a peptide containing "approximately" 50 amino acid residues can contain between 40 and 60 amino acid residues.

The term "binding composition" refers to molecules that bind with specificity to canine TSLP, e.g., in an antibody-antigen interaction. The specificity may be more or less inclusive, e.g., specific to a particular embodiment, or to groups of related embodiments, e.g., canine TSLP and/or canine antibodies.

As used herein the term, "canine" includes all domestic dogs, *Canis lupus* familiaris or *Canis familiaris*, unless otherwise indicated.

As used herein, the term, "polypeptide" is used interchangeably with the terms "protein" and "peptide" and denotes a polymer comprising two or more amino acids connected by peptide bonds. The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids, e.g., 35, 40, 45, 50, etc. Such fragments may have ends which begin and/or end at virtually all positions, e.g., beginning at residues 1, 2, 3, etc., and ending at, e.g., 155, 154, 153, etc., in all practical combinations.

Optionally, a polypeptide may lack certain amino acid residues that are encoded by a gene or by an mRNA. For example, a gene or mRNA molecule may encode a sequence of amino acid residues on the N-terminus of a polypeptide (i.e., a signal sequence) that is cleaved from, and therefore, may not be part of the final protein.

As used herein an amino acid sequence is 100% "homologous" to a second amino acid sequence if the two amino acid sequences are identical, and/or differ only by neutral or conservative substitutions as defined below. Accordingly, an amino acid sequence is about 80% "homologous" to a second amino acid sequence if about 80% of the two amino acid sequences are identical, and/or differ only by neutral or conservative substitutions.

Functionally equivalent amino acid residues often can be substituted for residues within the sequence resulting in a conservative amino acid substitution. Such alterations define the term "a conservative substitution" as used herein. For example, one or more amino acid residues within the sequence can be substituted by another amino acid of a similar polarity, which acts as a functional equivalent, resulting in a silent alteration. Substitutions for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred conservative substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. The amino acids also can be placed in the following similarity groups: (1) proline, alanine, glycine, serine, and threonine; (2) glutamine, asparagine, glutamic acid, and aspartic acid; (3) histidine lysine, and arginine; (4) cysteine; (5) valine, leucine, isoleucine, methionine; and (6) phenylalanine, tyrosine, and tryptophan.

In a related embodiment, two highly homologous DNA sequences can be identified by their own homology, or the homology of the amino acids they encode. Such comparison of the sequences can be performed using standard software available in sequence data banks. In a particular embodiment two highly homologous DNA sequences encode amino acid sequences having about 80% identity, more preferably about 90% identity and even more preferably about 95% identity. More particularly, two highly homologous amino acid sequences have about 80% identity, even more preferably about 90% identity and even more preferably about 95% identity.

As used herein, protein and DNA sequence percent identity can be determined using software such as MacVector v9, commercially available from Accelrys (Burlington, Mass.) and the Clustal W algorithm with the alignment default parameters, and default parameters for identity. See, e.g., Thompson, et al., 1994. *Nucleic Acids Res.* 22: 4673-4680. ClustalW is freely downloadable for Dos, Macintosh and Unix platforms from, e.g., EMBLI, the European Bioinformatics Institute. The present download link is found at http://www.ebi.ac.uk/clustalw/. These and other available programs can also be used to determine sequence similarity using the same or analogous default parameters.

A "polynucleotide" or a "nucleic acid molecule" is a molecule comprising nucleotides including, but is not limited to, RNA, cDNA, genomic DNA and even synthetic DNA sequences. The terms are also contemplated to encompass nucleic acid molecules that include any of the art-known base analogs of DNA and RNA.

The present invention provides nucleic acids that hybridize to nucleotide sequences encoding the TSLP proteins of the present invention. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength [see Sambrook and Russell, *Molecular Cloning, A laboratory Manual*, 3$^{rd}$ edition, Cold Spring Harbor Laboratory Press, Cold Spring Harbor L.I. (2000)].

High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived [see Sambrook and Russell, *Molecular Cloning, A laboratory Manual*, 3$^{rd}$ edition, Cold Spring Harbor Laboratory Press, Cold Spring Harbor L.I. (2000)]. For hybridization with shorter nucleic acids, i.e., oligonucleotides, the position of mismatches becomes more important, and the length of the oligonucleotide determines its specificity.

Preferably a minimum length for a hybridizable nucleic acid is at least about 12 nucleotides; more preferably at least about 18 nucleotides; even more preferably the length is at least about 24 nucleotides; and most preferably at least about 36 nucleotides. In a specific embodiment, the term "standard hybridization conditions" refers to a $T_m$ of 55° C., and utilizes conditions as set forth above. In another specific embodiment stringent conditions means the $T_m$ is 65° C. for both hybridization and wash conditions, respectively.

A DNA "coding sequence" or a "sequence encoding" a particular protein or peptide, is a DNA sequence which is transcribed and translated into a polypeptide in vitro or in vivo when placed under the control of appropriate regulatory elements.

The boundaries of the coding sequence are determined by a start codon at the 5'-terminus and a translation stop codon at the 3'-terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

A "heterologous nucleotide sequence" as used herein is a nucleotide sequence that is added to a nucleotide sequence of the present invention by recombinant methods to form a nucleic acid that is not naturally formed in nature. Such nucleic acids can encode fusion (e.g., chimeric) proteins. Thus the heterologous nucleotide sequence can encode peptides and/or proteins that contain regulatory and/or structural properties. In another such embodiment the heterologous nucleotide sequence can encode a protein or peptide that functions as a means of detecting the protein or peptide encoded by the nucleotide sequence of the present invention after the recombinant nucleic acid is expressed. In still another embodiment the heterologous nucleotide sequence can function as a means of detecting a nucleotide sequence of the present invention. A heterologous nucleotide sequence can comprise non-coding sequences including restriction sites, regulatory sites, promoters and the like.

As used herein the terms "fusion protein" and "fusion peptide" are used interchangeably and encompass "chimeric proteins and/or chimeric peptides" and fusion "intein proteins/peptides". A fusion protein comprises at least a portion of a canine TSLP protein of the present invention joined via a peptide bond to at least a portion of another protein, e.g. a non-canine TSLP protein, and/or comprises a combination of two or more noncontiguous portions of the canine TSLP protein, e.g., epitopes, that do not naturally occur in adjacent-sequential order in the canine TSLP polypeptide (e.g., a fusion peptide of ten amino acid residues that consists of amino acid residues 71-75 and 101-105 of SEQ ID NO: 2 combined in a peptide linkage). In preferred embodiments the portion(s) of the canine TSLP protein is functional, e.g., retains its antigenicity. Fusion proteins can also comprise a marker protein, or a protein that aids in the isolation and/or purification (e.g., a FLAG tag, see Examples below) and/or antigenicity of a canine TSLP protein of the present invention. The non-canine TSLP sequences can be amino- or carboxy-terminal to the canine TSLP sequences.

A recombinant DNA molecule encoding a fusion protein of the present invention, for example, can comprise a sequence encoding at least a portion of a non-canine TSLP protein joined in-frame to the canine TSLP coding sequence, and further can encode a cleavage site for a specific protease, e.g., thrombin or Factor Xa, preferably at or close to the juncture between the canine TSLP sequence and the non-canine TSLP sequence. In a specific embodiment, the fusion protein is expressed in a prokaryotic cell. Such a fusion protein can be used to isolate the canine TSLP of the present invention, through the use of an affinity column that is specific for the protein and/or a tag fused to the canine TSLP (see Examples below). The purified canine TSLP, for example, may then be released from the fusion protein through the use of a proteolytic enzyme and a cleavage site such as has been referred to above.

A "vector" or "replication vector" is a replicon, such as a plasmid, virus, phage, or cosmid, to which another DNA segment may be attached or incorporated so as to bring about the replication of the attached segment. The term also includes a replicon that includes the incorporated or attached DNA segment of interest.

Vectors that can be used in this invention include microbial plasmids, viruses, viruses, bacteriophage, integratable DNA fragments, and other vehicles that may facilitate integration of the nucleic acids into the genome of the host. Plasmids are the most commonly used vector, but all other vectors that serve an equivalent function and that are or become known in the art are suitable for use herein. [See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.]

Insertion of DNA encoding the inventive canine TSLP protein into a vector is easily accomplished when the termini of both the DNA and the vector comprise compatible restriction sites. If this cannot be done, it may be necessary to modify the termini of the DNA and/or vector by digesting back single-stranded DNA overhangs generated by restriction endonuclease cleavage to produce blunt ends, or to achieve the same result by filling in the single-stranded termini with an appropriate DNA polymerase. Alternatively, desired sites may be produced, e.g., by ligating nucleotide sequences (linkers) onto the termini. Such linkers may comprise specific oligonucleotide sequences that define desired restriction sites. Restriction sites can also be generated through the use of the polymerase chain reaction (PCR). See, e.g., Saiki et al., *Science* 239:487 (1988.). The cleaved vector and the DNA fragments may also be modified, if required, by homopolymeric tailing.

Recombinant expression vectors used in this invention are typically self-replicating DNA or RNA constructs comprising nucleic acids encoding a canine TSLP protein of the present invention and/or an antigenic fragment thereof usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors may also contain an origin of replication that allows the vector to replicate independently of the host cell.

Expression of nucleic acids encoding the inventive canine TSLP protein can be carried out by conventional methods in either prokaryotic or eukaryotic cells.

A "host cell" is a cell that contains, or is capable of containing, and expressing, an exogenous nucleic acid molecule, either transiently or permanently. A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cells containing the exogenous DNA.

Prokaryotes include both gram negative and positive organisms, e.g., *E. coli* and *B. subtilis*. Eukaryotes include established tissue culture cell lines from animal cells, both of non-mammalian origin, e.g., insect cells, and birds, and mammalian origin, e.g., human, primates, and rodents.

Prokaryotic host-vector systems include a wide variety of vectors for many different species Vectors for amplifying DNA include pBR322 or many of its derivatives, or the pET42b(+) expression vector (Novagen).

Prokaryotic expression control sequences typically used include promoters, including those derived from the β-lactamase and lactose promoter systems [Chang et al., *Nature*, 198:1056 (1977)], e.g., pUC-series, the tryptophan (trp) promoter system [Goeddel et al., *Nucleic Acids Res.* 8:4057 (1980)], e.g., (pBR322-trp), the lambda $P_L$ promoter system [Shimatake et al., *Nature*, 292:128(1981], lambda-pP or pR promoters (pOTS), arabinose-inducible promoters (InVitrogen), the tac promoter [De Boer et al., *Proc. Natl. Acad. Sci. USA* 292:128 (1983)], lpp promoter (the pIN-series); or hybrid promoters such as ptac (pDR540). Numerous other expression vectors containing such control sequences also are known in the art and are commercially available. [See also, Brosius et al., "Expression Vectors Employing Lambda-, trp-, lac-, and lpp-derived Promoters", in Rodriguez and Denhardt (eds.) *Vectors: A Survey of Molecular Cloning Vectors and Their Uses*, 1988, Buttersworth, Boston, pp. 205-236.]

Generically equivalent vectors to those appropriate for *E. coli*, which can be used in other prokaryotes, also may be used to express the TSLP proteins of the present invention.

Yeasts, as well as higher eukaryotic tissue culture cells are also contemplated as hosts for the recombinant production of the inventive canine TSLP protein, and/or of anti-canine TSLP antibodies and/or fragments of those antibodies. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, insect cell lines (e.g. SF9), bird cell lines (e.g. DF-11), Madin-darby bovine kidney (MDBK) cells, Madin-Darby canine kidney (MDCK) cell lines, Vero cells, HEK-293 cell lines and monkey (COS) cell lines.

Expression vectors for such cell lines usually include, for example, an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, paroviruses, vaccinia virus, or cytomegalovirus. Representative examples of suitable expression vectors include pCR®3.1, pCDNA1, pCD [Okayama et al., *Mol. Cell Biol.* 5:1136 (1985)], pMC1neo Poly-A [Thomas et al., *Cell* 51:503 (1987)], pUC19, pREP8, pSVSPORT and derivatives thereof, and baculovirus vectors, such as pAC 373 or pAC 610.

Once expressed, the inventive canine TSLP can be purified according to standard procedures to the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Purification can be partial, or to homogeneity as desired. If the canine TSLP is to be used therapeutically, the protein should be substantially free of endotoxin. Selective purification of expressed TSLP on a bound anti-TSLP antibody column, or on a bound TSLP-receptor column are available strategies for obtaining highly purified canine TSLP protein.

Methods for purification are well-known in the art. For example, nucleic acids can be purified by precipitation, chromatography, ultracentrifugation and other means. Proteins and polypeptides, as well as peptides, can be purified by various methods including, without limitation, preparative disc-gel electrophoresis, isoelectric focusing, HPLC, reversed-phase HPLC, gel filtration, ion exchange and partition chromatography, precipitation and salting-out chromatography, extraction and countercurrent distribution. For some purposes, it is preferable to produce the polypeptide in a recombinant system in which the protein contains an additional sequence tag that facilitates purification, such as, but not limited to, a polyhistidine sequence or a sequence that specifically binds to an antibody, such as FLAG® and GST. The polypeptide can then be purified from a crude lysate of the host cell by chromatography on an appropriate solid-phase matrix. Alternatively, antibodies, or binding fragments thereof produced against the polypeptide can be used as purification reagents.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS (cholesteryl hemisuccinate) or CHAPS (3-[3 cholamidopropyl) dimethylammoni-o]-1-propane sulfonate), or a low enough concentration as to avoid significant disruption of structural or physiological properties of the protein. In other instances, a harsh detergent may be used to effect significant denaturation.

Alternatively, functional heterologous proteins from $E.$ $coli$ or other bacteria can be isolated from inclusion bodies by means of solubilization using strong denaturants, and subsequent refolding. Art-known denaturants include, simply by way of example, urea, potassium thiocyanate, guanadine HCl ("GuHCl"), potassium iodate, and/or sodium iodide and combinations of these. Preferably, GuHCl is employed as a reducing agent, e.g., from about 6 to about 8 M in concentration, under alkaline conditions, e.g., about pH 8. Optionally another reducing agent, dithiothreitol ("DTT"), is employed, either alone or in combination with GuHCl. When DTT is employed, the concentration ranges, simply by way of example, from about 50 mM to about 0.5 mM DTT. During the solubilization step, as is well-known in the art, a reducing agent must be present to separate or denature the disulfide bonds. One exemplary reducing buffer is: 0.1 M Tris pH 8.0, 6 M guanidine, 2 mM EDTA, and 0.3 M DTE (dithioerythritol).

Renaturation is typically accomplished by dilution (e.g., 100-fold) of the denatured and reduced protein into a refolding buffer, in the presence of an oxidizing agent. Any suitable art-known oxidizing agent can be employed, provided that it allows for correct refolding in good yields. For example, oxidation and refolding can be provided by low molecular weight thiol reagents in reduced and oxidized form, as described in Saxena, et al., 1970, $Biochemistry$ 9: 5015-5021, incorporated by reference herein, and especially as described by Buchner, et al., supra. Renaturation is typically accomplished by dilution (e.g., 100-fold) of the denatured and reduced protein into a refolding buffer. One exemplary refolding buffer is: Tris HCl 100 mM, pH 10.0, 25 mM EDTA, NaCl 0.1 M, GSSG 551 mg/L, 0.5 M Arginine. GSSG is the oxidized form of glutathione.

The size and structure of the polypeptide should generally be in a substantially stable state, and usually not in a denatured state. The polypeptide may be associated with other polypeptides in a quaternary structure, e.g., to confer solubility, or associated with lipids or detergents.

Substantially pure, e.g., in a protein context, typically means that the protein is free from other contaminating proteins, nucleic acids, or other biologicals derived from the original source organism. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Carriers or excipients will often be added. Purity can be evaluated by chromatography, gel electrophoresis, immunoassay, composition analysis, biological assay and other methods known in the art. From a functional aspect, an isolated canine TSLP protein according to the invention is one sufficiently separated from other materials, including precursor canine TSLP protein and/or mature canine TSLP protein, so as to be capable of eliciting an immune response that is specific for the canine TSLP protein.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature is greater than about 18° C. For diagnostic purposes, the temperature will usually be about room temperature or warmer, but less than the denaturation temperature of components in the assay. For therapeutic purposes, the temperature will usually be body temperature, typically about 36° C. to 40° C. (e.g., about 39° C. for a dog) though under certain situations the temperature may be raised or lowered in situ or in vitro.

As used herein the term "antigenic fragment" in regard to a particular protein is a fragment of that protein (including large fragments that are missing as little as a single amino acid from the full-length protein) that is antigenic, i.e., capable of specifically interacting with an antigen recognition molecule of the immune system, such as an immunoglobulin (antibody) or T cell antigen receptor. For example, an antigenic fragment of the canine TSLP of the present invention is a fragment of the canine TSLP that is antigenic. Such fragments need not be itself immunogenic, i.e., capable of eliciting an immune response without a carrier, so long as they can be used to generate an antibody to the TSLP protein after conjugating the fragment to a carrier molecule for immunization. Preferably, however, an antigenic fragment of the present invention is immunodominant for antibody and/or T cell receptor recognition.

In a particular embodiment an antigenic fragment of the canine TSLP contains between 5 and 150 amino acid residues. In one particular embodiment the antigenic fragment of the canine TSLP contains greater than 120 amino acid residues. In another embodiment an antigenic fragment of the canine TSLP contains between 10 and 120 amino acid residues. In still another embodiment an antigenic fragment of the canine TSLP contains between 20 and 100 amino acid residues. In yet another embodiment an antigenic fragment of the canine TSLP contains between 25 and 75 amino acid residues.

An antigenic fragment of the canine TSLP can be obtained from a recombinant source, from a protein isolated from natural sources, or through chemical synthesis. Moreover, an antigenic fragment can be obtained following the proteolytic digestion of the canine TSLP, or a fragment thereof, through recombinant expression, or alternatively, it can be generated de novo, e.g., through peptide synthesis.

Vaccines

The present invention further provides vaccines that include an effective amount of a TSLP protein of the present invention, one or more antigenic fragments thereof, or combinations of the full-length protein and one or more of such fragments. For example, a canine TSLP protein and/or fragments thereof, such as those enumerated by Table 2, below, can be incorporated into any protein- or peptide-compatible vaccine composition. Such vaccine compositions are well known to the art and can, but do not necessarily include, for example, physiologically compatible buffers and saline and the like, as well as pharmaceutically acceptable adjuvants such as CARBOPOL® or Emulsigen®.

The vaccine composition can be employed for inducing endogenous anti-TSLP antibodies in a canine subject in need thereof, e.g., in order to treat clinical signs of a disease or disorder that is responsive to the downregulation of TSLP activity in a canine subject. Alternatively, or in conjunction therewith, a vaccine of the present invention also may be used to elicit antiserum for screening and/or identifying canine TSLP, e.g., as an aid in a test kit for identifying canines that overexpress TSLP.

Peptides of TSLP such as those disclosed in Table 2 below, and variants thereof, can be used as immunogens, either individually or in various combinations. Such peptides can be optionally linked to each other and/or to larger proteins known as carriers, either through chemical or recombinant DNA techniques. The carriers act to enhance peptide recognition by host animals as a target of the immune response and increase the immunogenicity of TSLP peptides. Several carriers are known in the art, and include tetanus toxoid or the non-toxic C fragment from tetanus toxin, diphteria toxoid, PhoP protein, keyhole limpet hemocyanin (KLH), beta galactosidase, gD protein from BHV-1 virus, G protein from rabies virus, F protein from canine distemper virus and synthetic carriers such as those produced by polymerization of known "universal" T cell epitopes.

TSLP peptides useful as immunogens can be selected from those in Table 2, and variants thereof, using known algorithms that evaluate attributes such as surface accessibility in the native TSLP protein, hydrophilicity, atomic mobility and antigenicity. Epitopes from peptides listed in Table 2, and variants thereof can also be selected based on their reactivity with polyclonal or monoclonal antibodies that react with native TSLP proteins and especially those antibodies that are capable of neutralizing TSLP bioactivity. Such antigens can include synthetic peptides prepared from the sequences disclosed herein employing standard peptide synthesis technology and/or alternatively, can be fragments obtained from recombinant or natural TSLP protein.

Pharmaceutically acceptable adjuvants of the present invention may be obtained from any of a number of sources including from natural sources, recombinant sources, and/or be chemically synthesized, etc. Examples of chemical compounds used as adjuvants include, but are not limited to aluminum compounds, metabolizable and non-metabolizable oils, block polymers, ISCOM's (immune stimulating complexes), vitamins and minerals (including but not limited to: vitamin E, vitamin A, selenium, and vitamin B12), and Quil A (saponins), Freund's complete adjuvant, polymers of acrylic acid cross-linked with polyalkenyl ethers or divinyl glycol, as sold under the trademark CARBOPOL® (e.g., CARBOPOL® 941), and a uniformly dispersed micron size oil droplets in water emulsion (e.g., as sold under the trademark Emulsigen®). Additional examples of adjuvants, that sometimes have been referred to specifically as immune stimulants, include, bacterial and fungal cell wall components (e.g., lipopolysaccharides, lipoproteins, glycoproteins, muramylpeptides, beta-1,3/1,6-glucans), various complex carbohydrates derived from plants (e.g., glycans, acemannan), various proteins and peptides derived from animals (e.g., hormones, cytokines, co-stimulatory factors), and novel nucleic acids derived from viruses and other sources (e.g., double stranded RNA, CpG). In additions any number of combinations of the aforementioned substances may provide an adjuvant effect and therefore, can form an adjuvant of the present invention.

The vaccines of the present invention may be administered by any route including: intramuscular injection, subcutaneous injection, intravenous injection, intradermal injection, oral administration, intranasal administration, and combinations thereof.

Antibodies

The present invention also includes polyclonal and monoclonal (mAb) antibodies that specifically bind to the inventive canine TSLP protein. As used herein, the term "antibody" refers to an immunoglobulin and/or fragments thereof. A naturally occurring immunoglobulin consists of one or more polypeptides substantially encoded by immunoglobulin genes. The recognized immunoglobulin genes include the kappa, lambda, alpha, gamma, delta, epsilon and mu constant region genes, as well as the myriad of immunoglobulin variable region genes. An antibody or antibodies according to the invention also encompass antibody fragments, i.e., antigen-binding fragments, for example, Fv, Fab, and F(ab')$_2$, engineered single-chain binding proteins, e.g., Huston et al., *Proc. Natl. Acad. Sci. U.S.A.*, 85, 5879-5883 (1988) and Bird et al., *Science*, 242, 423-426 (1988), incorporated herein by reference herein), as well as bifunctional hybrid antibodies (e.g., Lanzavecchia et al., *Eur. J. Immunol.* 17, 105 (1987)). See, generally, Hood et al., Immunology, Benjamin, N.Y., 2nd ed. (1984), Harlow and Lane, *Antibodies. A Laboratory Manual*, Cold Spring Harbor Laboratory (1988) and Hunkapiller and Hood, *Nature*, 323, 15-16 (1986), all of which are incorporated by reference herein.

For example, serum produced from animals immunized by the inventive canine TSLP protein, using standard methods, can be used directly, or the IgG fraction can be separated from the serum using standard methods, such as plasmaphoresis or adsorption chromatography with IgG-specific adsorbents, such as immobilized Protein A or Protein G. Alternatively, monoclonal antibodies can be prepared, and optionally, antigen binding fragments or recombinant binding proteins derived from such mAbs. Such MAbs or fragments thereof can optionally be humanized, or caninized by art-known methods or straightforward modifications thereof, respectively.

As used herein, an "epitope-specific" canine TSLP antibody is an antibody that is raised against a fragment of canine TSLP that comprises an epitope comprising one or more of the following five amino acid sequences. SEQ ID NO: 30, SEQ ID NO: 31 SEQ ID NO: 32, SEQ ID NO: 33, and SEQ ID NO: 34; and that further binds a protein having the amino acid sequence of SEQ ID NO: 2, and/or a protein having the amino acid sequence of SEQ ID NO: 2, excluding the 28 amino acid residue signal sequence. In a particular embodiment, the epitope-specific canine TSLP antibody is a monoclonal antibody.

Hybridomas producing mAbs that selectively bind the canine TSLP protein of the invention are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and, in general, involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay) or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al., *Hybridoma Techniques* (Cold Spring Harbor Laboratory, New York, 1980); Tijssen, *Practice and Theory of Enzyme Immunoassays* (Elsevier. Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)]. Monoclonal antibodies can also be produced using well-known phage library systems. [See, e.g., Huse, et al., *Science* 246:1275 (1989); Ward, et al., *Nature,* 341:544 (1989)].

Antibodies thus produced, whether polyclonal or monoclonal, can be used, e.g., in an immobilized form bound to a solid support by well known methods to purify the canine TSLP protein by immunoaffinity chromatography.

Antibodies against the canine TSLP protein can also be used, unlabeled or labeled by standard methods, as the basis for immunoassays to detect or quantify canine TSLP protein. The particular label used will depend upon the type of immunoassay. Examples of labels that can be used include, but are not limited to, radiolabels, such as $^{32}P$, $^{125}I$, $^3H$ and $^{14}C$; fluorescent labels, such as fluorescein and its derivatives, rhodamine and its derivatives, dansyl and umbelliferone; chemiluminescers, such as luciferin and 2,3-dihydrophthalazinediones; and enzymes, such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing canine TSLP protein in expression cloning systems. Neutralizing antibodies specific for the ligand-binding site of a receptor can also be used as antagonists (inhibitors) to block or downregulate canine TSLP protein function. Such neutralizing antibodies readily can be identified through routine experimentation.

Antagonism of canine TSLP protein activity can be accomplished using complete antibody molecules, or well-known antigen binding fragments such as Fab, Fc, $F(ab)_2$, and Fv fragments. Definitions of such fragments can be found as described hereinabove, or e.g., in Klein, *Immunology* (John Wiley, New York, 1982); Parham, Chapter 14, in Weir, ed. *Immunochemistry,* 4th Ed. (Blackwell Scientific Publishers, Oxford, 1986). The use and generation of antibody fragments has also been described, e.g. Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Pluckthun [*Bio/Technology* 9:545 (1991)]. Alternatively, they can be chemically synthesized by standard methods.

The present invention also encompasses anti-idiotypic antibodies, both polyclonal and monoclonal, which are produced using the above-described antibodies as antigens. These antibodies are useful because they may mimic the structures of the ligands.

Antibodies generated from non-canine mammals or non-canine hybridoma systems can optionally be engineered in order to render them substantially nonantigenic when injected into canines, i.e., they may be caninized. The process of modifying a monoclonal antibody from an animal to render it less immunogenic for therapeutic administration to humans (humanization) has been aggressively pursued and has been described in a number of publications [e.g. *Antibody Engineering: A practical Guide*. Carl A. K. Borrebaeck ed. W.H. Freeman and Company, 1992; Reichman, L. et al., "Reshaping human antibodies for therapy", *Nature* 332; 323-327 (1988)]. Alternatively, monoclonal antibodies from non-canine mammals, e.g., mouse monoclonal antibodies, are chimerized with canine antibodies or sequences thereof so as to achieve antibodies which are seen to the recipient host as less immunogenic than standard murine monoclonal antibodies. See e.g., U.S. Pat. No. 5,593,861, "Dog-Mouse Heterohybridoma and Gene Fragment Coding for Constant Region of Canine Immunoglobulins", which is incorporated herein by reference.

In addition, Wasserman and Capra, [*Biochem.* 16: 3160 (1977)] determined the amino acid sequence of the variable regions of both a canine IgM and a canine IgA heavy chain. These workers further determined the amino acid sequence of the kappa light chain from a canine IgA [Wasserman and Capra, *Immunochem.* 15: 303 (1978)]. McCumber and Capra, [*Mol. Immunol.* 16: 565 (1979)] disclose the complete aminoacid sequence of a canine mu chain. Tang et al., [*Vet. Immunology Immunopathology* 80: 259 (2001)], disclose a single canine IgG-A gamma chain cDNA and four canine IgG-A gamma chain protein sequences. Tang et al., supra, further describe PCR amplification of a canine spleen cDNA library with a degenerate oligonucleotide primer designed from the conserved regions of human, mouse, pig, and bovine IgGs. Moreover, Krah, et al. [U.S. Publication No. 20040181039, published on Sep. 16, 2004 and incorporated by reference herein] describe in detail one process for caninizing non-canine antibodies.

Isolation of the Canine TSLP Gene

A. Initial Attempts

The initial attempts to identify canine TSLP were based on sequence alignments of cloned Human, and Mouse TSLP cDNA sequences with the Rat, Chimpanzee and Rhesus TSLP cDNA sequences that were assembled from BLAT (public genomic database University of California, Santa Cruz). Chimpanzee TSLP is 100% identical to human TSLP at the amino acid level, whereas Rhesus TSLP has over 90% homology with human TSLP (12/151 residue different) in the mature protein. However, the human and non-human primate TSLP protein and cDNA sequences are highly divergent from murine TSLP sequences. The human and mouse TSLP cDNA sequences only comprise 43% homology, which does not allow cloning through low stringency cross-species hybridization between these species. Furthermore, the Rat TSLP sequence showed 39/121 changes in amino acid residue sequence of the mature protein as compared to mouse TSLP indicating that even between closely related murine species the TSLP sequences have diverged significantly.

Unfortunately, as disclosed herein, the canine TSLP sequence also proved to be divergent from all of the disperate murine and the similar primate sequences. Therefore, obtaining canine TSLP through low stringency cross-species hybridization proved unsuccessful. Indeed, primers designed in an attempt to clone out the canine TSLP ortholog in nested PCR strategies employing the human, mouse, rat and monkey sequence information failed to identify even a single band that corresponded to canine TSLP.

B. Successful Isolation of Canine TSLP Gene

Searching the then available assembled canine genomic database (derived from whole genome shotgun sequencing; made available to the public by the University of California, Santa Cruz) with the human TSLP sequence led to the partial identification of exon 1 and 4 of canine TSLP. Briefly, several hits of significant sequence homology were identified in this initial search (See "hits" 1-6, below). Their sequences were collected and used as queries to extend and assemble a partial electronic sequence of the canine TSLP gene.

```
Hit 1

Score = 60.8 bits (146), Expect = 1e - 08
Identities = 33/58 (56%), Positives = 39/58 (67%) Gaps 1/58 (1%)

Query:    7 LYVLSVS-FRKIFILQLVGLVLTYDFTNCDFEKIKAAYLSTISKDLITYMSGTKSTEF    63
            L + SVS FRKIF+LQLVGLVLTY+F +CDFEKI+  Y    I + L   YM G      F
Sbjct:   26 LITCSVSVFRKIFVLQLVGLVLTYNFIDCDFEKIRWKYQEVIYQALEKYMDGVSE*TF   199

SEQ ID NO: 102; human TSLP
SEQ ID NO: 103; >gi|36323560|gb|AACN010632090.1| Canis familiaris
ctg19866851299046, whole genome shotgun sequence Length = 1007

Hit 2:

Score = 59.7 bits (143), Expect = 3e - 08
Identities = 30/42 (71%) Positives 33/42 (78%)
Frame = -1

Query: 117 QINATQAMKKRRKRKVTTNKVLEQVSQLQGWRRFNRPLLQK              158 (SEQ ID NO: 104)
           QIN TQA KKR+KR VTTNKC EQV +L GLWRRF+R    KQ
Sbjct: 588 QINNTQAKKKRKKRGVTTNKVREQVAHLIGLWRRFSRIS*KQ              463 (SEQ ID NO: 105)

SEQ ID NO: 104 human TSLP
SEQ ID NO: 105 >gi|36314527|gb|AACN010674832.1 Canis familiaris
ctg19866851282529, whole genome shotgun sequence Length = 963
```

-continued

```
Hit 3

Score = 42.0 bits (97), Expect = 0.006
Identities = 21/44 (47%), Positives = 27/44 (61%)
Frame = -2

Query:  76 LTEIQSLTFNPTAGCASLAKEMFAMKTKAALAIWCPGYSETQIN      119 (SEQ ID NO: 106)
           L  I+ LT +   GCAS A+E FA  T AALA  CPGY+   --
Sbjct: 369 LARIERTLHRIRGCASGAREAFAEGTVAALAAECPGYAAAPVS      238 (SEQ ID NO: 107)

SEQ ID NO: 106: human TSLP
SEQ ID NO: 107 >gi|36442813|gb|AACN011084208.1| Canis familiaris
ctg19866851499233, whole genome shotgun sequence Length = 370

Hit 4

Score = 38.9 bits (89), Expect = 0.047
Identities = 15/32 (46%), Positives 22/32 (68%)
Reading Frame = +1

Query:  87 TAGCASLAKEMFAMKTKAALAIWCPGYSETQI                 118 (SEQ ID NO: 108)
           T GC   AKE A+    AL++WCPG+++TQ+
Sbjct: 178 TPGCGICAKEAAALGWFCALSVWCPGWAQTQV                 273 (SEQ ID NO: 109)

SEQ ID NO: 108: human TSLP
SEQ ID NO: 109 >gi|36211043|gb|AACN010354273.1| Canis familiaris
ctg19866851087147, whole genome shotgun sequence Length = 1369

Hit 5

Score = 42.0 bits (97), Expect = 0.006
Identities = 21/44 (47%), Positives 27/44 (61%)
Reading Frame = -2

Query:  76 LTEIQSLTFNPTAGCASLAKEMFAMKTKAALAIWCPGYSETQIN      119 (SEQ ID NO: 110)
           L  I+ LT +   GCAS A+E FA  T AALA  CPGY+   ++
Sbjct: 369 LARIERLTHRIRGCASGAREAFAEGTVAALAAECPGYAAAPVS      238 (SEQ ID NO: 111)

(SEQ ID NO: 110: human TSLP
SEQ ID NO: x111 >gi|36211043|gb|AACN010354273.1| Canis familiaris
ctg19866851087147, whole genome shotgun sequence Length = 1369

Hit 6

Score = 38.9 bits (89), Expect = 0.047
Identities = 15/32 (46%), Positives = 22/32 (68%)
Frame = +1

Query:  87 TAGCASLAKEMFAMKTKAALAIWCPGYSETQI                 118 (SEQ ID NO: 112)
           T GC   AKE A+    AL++WCPG+++TQ+
Sbjct: 178 TPGCGICAKEAAALGWFCALSVWCPGWAQTQV                 273 (SEQ ID NO: 113)

SEQ ID NO: 112: human TSLP
SEQ ID NO: 113: >gi|36211043|gb|AACN010354273.1| Canis familiaris
ctg19866851087147, whole genome shotgun sequenc Length = 1369
```

A comparison of this electronically constructed sequence with human, monkey, rat, and mouse TSLP demonstrated the conserved intron/exon borders and substantial sequence identity, leading to the identification of this sequence as part of the canine ortholog of TSLP. PCR primers were subsequently designed based on this discovery and used to amplify the missing segments of the gene. Two partial overlapping clones were obtained by double nested PCR from a canine activated peripheral blood mononuclear cells (PBMC) cDNA library. Additional attempts to uncover the full canine TSLP cDNA by nested PCR or trying to extend sequences towards the 5' or 3' ends were not successful. However, iterative rounds of database searches using the extended sequence information from these clones on the canine whole genome shotgun sequence data (Id. University of California Santa Cruz) combined with manual assembly of the raw DNA sequence from this library led to the electronic assembly of the full length canine TSLP cDNA. A physical clone of this cDNA sequence was then synthesized using a DNA synthesizer, in vitro.

In conclusion, using current and state of the art molecular cloning techniques it was not possible to derive the canine TSLP sequence directly from the human, mouse, rat or monkey sequences. Only sophisticated iterative database searches using assembled human, mouse, rat and NHP TSLP genes, with use of intron/exon boundary assignments and sequence identity on genomic databases, combined with molecular PCR cloning techniques, led to identification of the gene encoding canine TSLP.

Once obtained, the canine TSLP showed 58/132 changes compared to the amino acid sequence of the mature human TSLP protein (61% identity) and 83/129 changes compared to the amino acid sequence of the mature mouse TSLP protein (33% identity) (see below).

| Sequence Comparison Between *Canis familiaris* and Human TSLP Mature Protein |
| --- |
| TSLP_CF (*Canis familiaris*)   Length 141 (1 . . . 141) |
| TSLP_H (Human)   Length 145 (1 . . . 145) |
| Score = 167 bits (423), Expect = 1e - 40<br>Identities = 85/139 (61%),<br>Positives = 101/139 (72%) |
| Query:   1 RKIFVLQLVGLVLTYNFIDCDFEKIRWKYQEVIYQALEKYMDGTRSTEFSHPVYCANPPD  60<br>            RKIF+LQLVGLVLTY+F +CDFEKI+    Y     I + L    YM GT+STEF++ V C+N P<br>Sbjct:   1 RKIFILQLVGLVLTYDFTNCDFEKIKAAYLSTISKDLITYMSGTKSTEFNNTVSCSNRPH  60 |
| Query:  61 CLARIERLTLHRIRGCASGAREAFAEGTVAALAAECPGYAAAPINNTQAKKKRKKRGVTT 120<br>            CL  I+ LT +    GCAS A+E FA   T AALA  CPGY+    IN TQA KKR+KR VTT<br>Sbjct:  61 CLTEIQSLTFNPTAGCASLAKEMFAMKTKAALAIWCPGYSETQINATQAMKKKRRKRKVTT 120 |
| Query: 121 NKCREQVAHLIGLWRRFSR                                         139 (SEQ ID NO: 114)<br>            NKC EQV+ L GLWRRF+R<br>Sbjct: 121 NKCLEQVSQLQGLWRRFNR                                         139 (SEQ ID NO: 115) |
| SEQ ID NO: 114: *Canine familiaris* TSLP<br>SEQ ID NO: 115: Human TSLP |

| Sequence Comparison Between *Canis familiaris* and Murine TSLP Mature Protein |
| --- |
| TSLP_CF                                                  Length 141 (1 . . . 141) |
| TSLP_M                                                   Length 135 (1 . . . 136) |
| Score = 72.0 bits (175), Expect = 7e - 12<br>Identities = 46/138 (33%), Positives = 67/138 (48%), Gaps = 8/138 (5%) |
| Query:   1 RKIFVLQ-LVGLVLTYNFIDCDFEKIRWKYQEVITYQALEKYMDGTRSTEFSHPVYCANPP  59<br>            R +F+LQ L V+ LTYNF +C+F  I    Y  +I+   L    + G+  +      C + P<br>Sbjct:   1 RSLFILQVLVRMGLTYNFSNCNFTSITKIYCNIIFHDLTGDLKGAKFEQIED---<br>                 CESKP                                                      57 |
| Query:  60 DCLARIERLTLHRIRGCASGAREAFAEGTVAALAAEGPGYAAAPINNTQAKKKRKKRGVT 119<br>              CL +IE  TL+ I GC S  + FA  T  AL   CPGY       N+   +  ++<br>Sbjct:  58 ACLLKTEYYTLNPIPGCPSLPDCKTFARRTREALNDHCPGYPETERNDGTQEMAQE----V 113 |
| Query: 120 TNKCRQQVAHLIGLWRRF                                         137 (SEQ ID NO: 116)<br>             N C  Q + ++ LW  F<br>Sbjct: 114 QNICLNQTSQILRLWYSF                                         131 (SEQ ID NO: 117) |
| SEQ ID NO: 116: *Canine familiaris* TSLP<br>SEQ ID NO: 117: Mouse TSLP |

Thus, by overcoming the previously noted difficulties, the present invention now provides DNA sequences encoding canine TSLP and the encoded canine TSLP protein. Canine TSLP protein and certain fragments thereof are useful antigens, e.g., immunogens, for raising antibodies to various epitopes on the protein, both linear and conformational epitopes. The DNA encoding canine TSLP is also useful in providing vectors and host cells for producing TSLP protein for immunization and/or as a research reagent, as well as providing DNA-based vaccines for raising anti-TSLP antibodies, whether as "naked" DNA or in the form of a plasmid or animal virus vector suitable for expressing TSLP in the cells of a vaccinated animal.

The thus obtained canine TSLP gene sequence is illustrated by FIG. 8A (SEQ ID NO: 1), and the predicted expressed TSLP protein is illustrated by FIG. 8B (SEQ ID NO: 2). Residues 1-28 represent the signal sequence, and residues 29 to 155 represent the mature protein.

Assay for Identifying Homologous TSLP Proteins

The present invention also provides TSLP proteins that comprise an amino acid sequence that has 80% or greater identity to the amino acid sequence of SEQ ID NO: 2, excluding the 28 amino acid residue signal sequence, which when they are administered to a canine as a vaccine, raise antibodies that bind the canine TSLP protein comprising the amino acid sequence of SEQ ID NO: 2. Antigenic fragments of such TSLP proteins are also provided.

Indeed, one way to demonstrate that a putative TSLP protein is a TSLP of the present invention is to test whether such a protein can generate antibodies that bind to canine TSLP comprising the amino acid sequence of SEQ ID NO: 2. One such method is to vaccinate (e.g., inject) dogs with various doses ranging from 5-500 µg of a putative TSLP-GST antigen. Such antigens can be formulated in an aluminum hydroxide-based adjuvant such as Rehydrogel. The dogs are then injected intramuscularly three times: at day 0, day 21, and day 42. Serum samples are collected from vaccinated and control (non-immunized) dogs on days 0, 21, 42, and 63.

The induction of antibodies in dogs vaccinated with the antigens can be evaluated with an ELISA assay as follows: canine TSLP protein comprising the amino acid sequence of SEQ ID NO: 2 is diluted to 5 µg/ml in coating buffer (Sodium Bicarbonate pH 9.0) and dispensed at 100 µl/well of 96 well plates (Pierce). The plates are incubated at 4° C. overnight. Next the plates are washed three times with phosphate buffer saline containing 0.05% Tween-20 (PBST). Then, 200 µl of blocking buffer (2% skim milk in PBST) is added to each well and the plates are incubated at room temperature for 60 minutes. The plates are then washed three times with PBST. Next, 100 µl/well of 1:100 dilution of the test dog antisera is added to the top row of the appropriate wells. Serum samples are then diluted 10 fold to the appropriate plate position. Following the incubation of the plates at room temperature for 60 minutes, the plates are washed three times with PBST.

Next, 100 µl/well of a 1:20,000 dilution of a horse-radish peroxidase conjugated goat anti-dog IgG (Bethyl Laboratories) is added to each well. Then the plates are incubated at room temperature for 60 minutes. Next the plates are washed three times with PBST, and 100 µl/well of TMB substrate (3,3',5,5' tetramethyl benzidine, Sigma Chemical Co., St. Louis, Mo.) is then added to all wells. The color reaction is allowed to develop for 10-20 minutes at room temperature prior to being stopped by adding 50 µl/well of 0.18 M sulfuric acid.

The optical density (O.D.) of all of the wells is determined at the wavelength of 450 nm using an ELISA plate reader (Thermo Max; Molecular Devices, Sunnyvale, Calif.), Serum samples obtained from canines injected with the putative TSLP antigens are considered detectable and thereby, the antigens are identified as TSLP proteins of the present invention when the assay produces an O.D. value equal to or more than three times the background produced by serum samples obtained from the dogs prior to immunization. Similarly, relative antibody titers for the TSLP antigens can be determined based on the highest serum dilution producing an O.D. value equal to or more than three times the background produced by serum samples obtained from dogs prior to the immunization with the antigens.

Antibodies to Specific Epitopes of Canine TSLP Protein

Antibodies can be raised to various epitopes of the canine TSLP proteins, including species, polymorphic, or allelic variants, and fragments thereof, both in their naturally occurring forms and in their recombinant forms. Additionally, antibodies can be raised to canine TSLPs in either their active forms or in their inactive forms, including native or denatured versions. Anti-idiotypic antibodies are also contemplated.

Antibodies, including binding fragments and single chain versions, against predetermined fragments of the antigens can be raised by immunization of animals with canine TSLP and/or fragments thereof, together with art-standard adjuvants and/or conjugated to immunogenic proteins. Animals so immunized can be canines that are immunized in order to downregulate canine TSLP activity.

An appropriate host, e.g., an inbred strain of mice such as Balb/c, is immunized with the selected protein, typically using a standard adjuvant, and a standard mouse immunization protocol (see Harlow and Lane, Id. supra). An adjuvant may be administered to the target animal before, in combination with, or after the administration of the vaccine.

Alternatively, a synthetic peptide derived from the sequences disclosed herein and conjugated to a carrier protein can be used an immunogen. Polyclonal sera are collected and titered against the immunogen protein in an immunoassay, e.g., a solid phase immunoassay with the immunogen immobilized on a solid support. Polyclonal antisera with a titer of $1 \times 10^4$ or greater are selected and tested for their cross reactivity against other IL-7 family members, e.g., rodent IL-7, using a competitive binding immunoassay such as the one described in Harlow and Lane. Id. supra, at pages 570-573. Preferably at least one other IL-7 family member is used in this determination in conjunction with e.g., the primate IL-7. The IL-7 family members can be produced as recombinant proteins and isolated using standard molecular biology and protein chemistry techniques as described herein.

Immunoassays in the competitive binding format can be used for the crossreactivity determinations. For example, the protein of SEQ ID NO. 2 can be immobilized to a solid support. Proteins added to the assay compete with the binding of the antisera to the immobilized antigen. The ability of the above proteins to compete with the binding of the antisera to the immobilized protein is compared to the protein comprising the amino acid sequence of SEQ ID NO: 2. The percent crossreactivity for the above proteins is calculated employing standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein to the immunogen protein (e.g., the IL-7 like protein of SEQ ID NO: 2). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of the selected protein or proteins that is required, then the second protein is said to specifically bind to an antibody generated to the immunogen.

The antibodies of this invention can also be useful in diagnostic applications. As capture or non-neutralizing antibodies, they can be screened for ability to bind to the antigens without inhibiting binding to a receptor. As neutralizing antibodies, they can be useful in competitive binding assays. They will also be useful in detecting or quantifying canine TSLP protein or its receptors. [See, e.g., Chan (ed. 1987) *Immunology: A Practical Guide*, Academic Press, Orlando, Fla.; Price and Newman (eds. 1991) *Principles and Practice of Immunoassay*, Stockton Press, N.Y.; and Ngo (ed. 1988) *Nonisotopic Immunoassay*, Plenum Press, N.Y.] Cross absorptions, depletions, or other means will provide preparations of defined selectivity, e.g., unique or shared species specificities. These may be the basis for tests which will identify various groups of antigens.

Further, the antibodies, including antigen binding fragments, of this invention can be potent antagonists that bind to the antigen and inhibit functional binding, e.g., to a receptor which may elicit a biological response. Further, these antibodies can be conjugated to drugs or other therapeutic agents, either directly or indirectly by means of a linker, and may effect drug targeting.

A synthetic peptide derived from the sequences disclosed herein and conjugated to a carrier protein can be used an immunogen. In any case, antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York; Williams, et al. (1967) *Methods in Immunology and Immunochemist*, vol. 1, Academic Press, New York; and Harlow and Lane (1988) *Antibodies: A Laboratory Manual*, CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.), Academic Press, New York; and particularly in Kohler and Milstein (1975) in *Nature* 256:495-497, which discusses one method of generating monoclonal antibodies.

Other suitable techniques involve in vitro exposure of lymphocytes to the antigenic polypeptides or alternatively to selection of libraries of antibodies in phage or similar vectors. [See, Huse, et al. (1989) "Generation of a Large Combinatorial Library of the Immunoglobulin Repertoire in Phage Lambda," *Science* 246:1275-1281; and Ward, et al. (1989) *Nature* 341-544-546.] The polypeptides and antibodies of the present invention may be used with or without modification, including chimeric, caninized, and/or humanized antibodies.

Frequently, the polypeptides and antibodies of the present invention will be labeled by joining a substance which provides for a detectable signal. Such joining can be accomplished either covalently or non-covalently. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850, 752; 3,939,350; 3,996,345; 4,277,437; 4,275,149; and 4,366, 241. Also, recombinant or chimeric immunoglobulins may be produced, see Cabilly, U.S. Pat. No. 4,816,567; Moore, et al., U.S. Pat. No. 4,642,334; and Queen, et al. (1989) *Proc. Nat'l. Acad. Sci. USA* 86: 10029-10033; or made in transgenic mice, see Mendez, et al. (1997) *Nature Genetics* 15:146-156. These references are incorporated herein by reference.

The antibodies of this invention can also be used for affinity chromatography in isolating the protein. Columns can be prepared where the antibodies are linked to a solid support, (see, e.g., Wilchek et al. (1984) *Meth. Enzymol.* 104:3-55). Alternatively, antigens bound to a solid support may be used to purify the corresponding antibodies.

Antibodies raised against each canine TSLP will also be useful to raise anti-idiotypic antibodies. These will be useful in detecting or diagnosing various immunological conditions related to expression of the respective antigens.

RNA Inhibition

Interference with RNA encoding canine TSLP in cells producing canine TSLP is an additional means of inhibiting the biological activity of TSLP and consequently, treating a number of TSLP-associated disorders such as atopic dermatitis. For this purpose, double stranded RNA molecules either synthesized chemically or cloned within appropriate delivery vectors such as plasmids or viral vectors may be introduced into cells actively producing TSLP mRNA with the aim of reducing endogenous mRNA levels encoding TSLP. Following entry of these RNA molecules (in the case of exogenously delivered molecules or transcription of RNA following entry of plasmids or viral vectors into desired cells), they are processed through the cleavage activity of a ribonuclease III-type protein into short nucleotide fragments which are termed siRNA. These siRNA fragments are then incorporated into a nuclease-containing multi-protein complex called RISC (RNA-Induced Silencing Complex), which becomes activated as a result of the unwinding of the siRNA duplex through the activity of an RNA helicase. The now single stranded siRNA strand guides the RISC complex to its target mRNA, which is then cleaved and subsequently degraded by the endonucleolytic activity of RISC.

More particularly, plasmids containing the TSLP gene or fragment thereof are cloned in any one of a number of commercially available eucaryotic plasmids wherein the transcription of the TSLP gene or its fragments is driven by an appropriate promoter, e.g., the CMV or SV40 promoter. Purified plasmid DNA (1-100 ug) is then injected into skin lesions or into areas surrounding the skin lesions characteristic of atopic dermatitis. The injection of plasmid DNA may then be repeated on a frequency necessary to cause a significant reduction in TSLP mRNA. This reduction may be evaluated by obtaining skin biopsies from affected areas and determining the level of TSLP mRNA by methods such as quantitative PCR.

The following preparative examples of the present invention serves to provide further appreciation of the invention, but are not meant in any way to restrict the effective scope of the invention.

EXAMPLES

Example 1

The Canine TSLP DNA and Protein Sequences

A canine gene expressing canine TSLP was identified by an iterative process employing data mining in electronic data bases and molecular biology methods, as described in detail supra.

Results

The canine TSLP gene sequence is illustrated by FIG. 8A (SEQ ID NO: 1), and the predicted protein expressed TSLP protein is illustrated by FIG. 8B (SEQ ID NO: 2). Residues 1-28 of FIG. 8B (SEQ ID NO: 2) marked by the asterisk, represent the signal sequence, and residues 29 to 155 represent the mature protein.

Example 2

Cloning and Expression of Canine TSLP

The DNA encoding canine TSLP was identified as described herein and cloned into a donor vector art standard methods pDONR221 (Invitrogen Gateway System). Gene assembly and cloning into the donor vector was performed at a contract research organization called DNA 2.0, and resulted in the construction of a plasmid called pDONR221.G03276 which contains the identified genomic canine TSLP gene. DNA encoding mature (i.e. without signal sequence) canine TSLP protein was PCR-amplified from pDONR221G03276 using two primers which contain Nco I and EcoR V sites, respectively:

```
Primers
                                       (SEQ ID NO: 4)
#1:  5' AATAATCCATGGCATACAATTTCATTGACTGTGAC-3';
and (SEQ ID NO: 5)
2:  5'-AAAATAGATATCTGAAATGCGACTGAAACGACG-3'.
```

Figure 1:
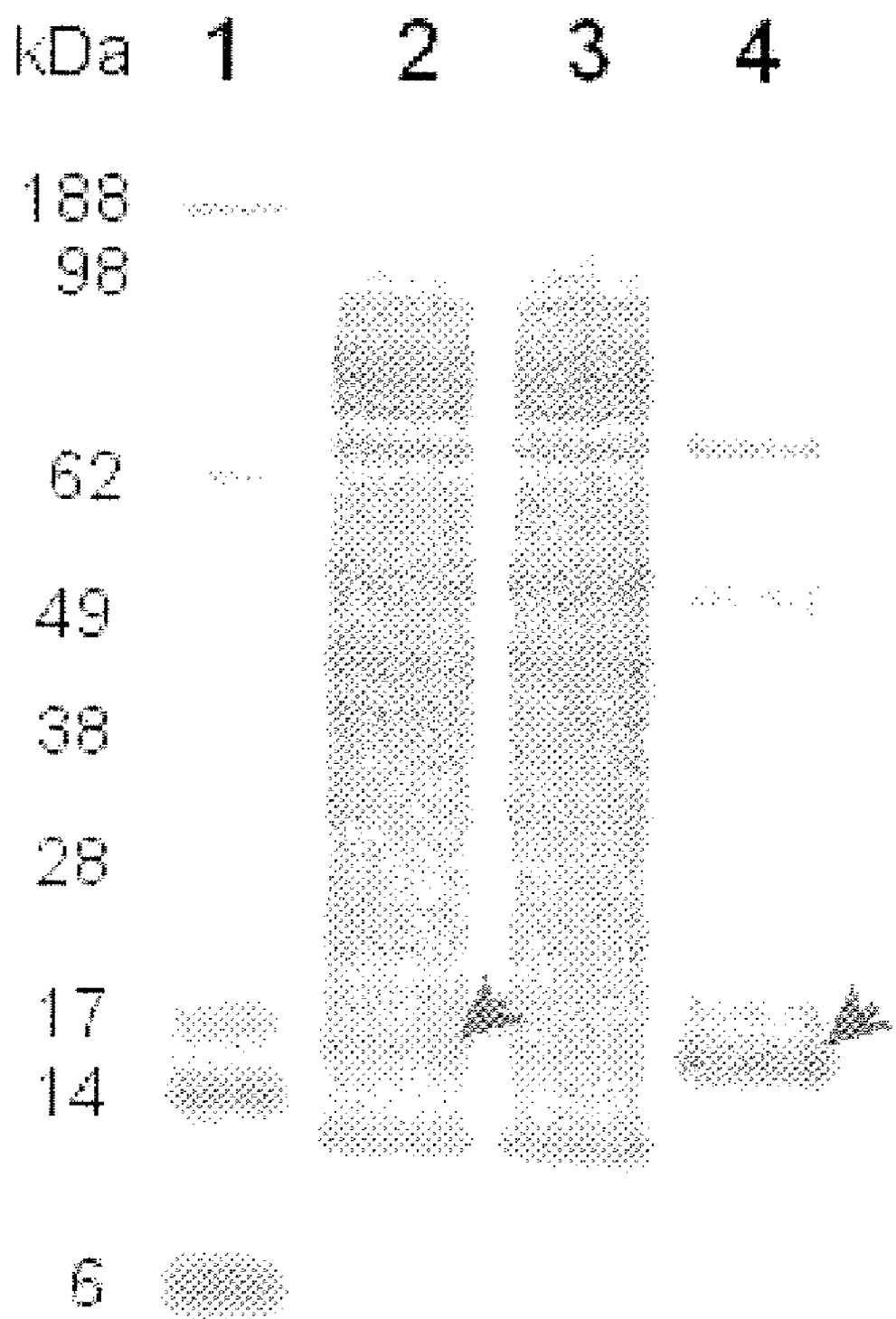
FIG. 1 illustrates SDS-PAGE analysis of protein from eukaryotic cell-free protein synthesis system expressing canine TSLP protein. Lane 1: Protein standard; Lane 2: Total protein; Lane 3: Soluble protein; Lane 4: Insoluble protein. TSLP protein bands are indicated by arrows.
Figure 2A:
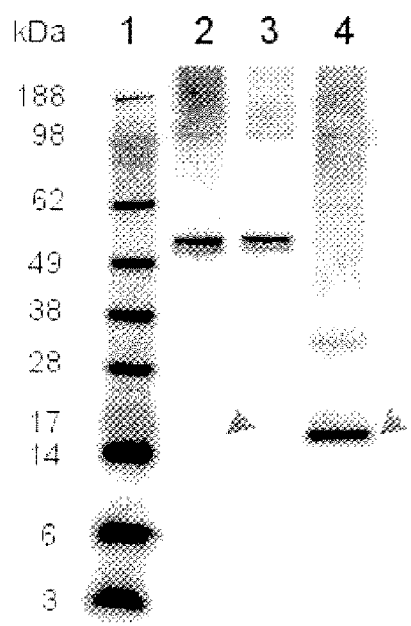
FIG. 2A illustrates Western blot analysis of protein from eukaryotic cell-free protein synthesis system expressing canine TSLP protein. The protein was reacted with Anti-His (C Term)/AP Ab from Invitrogen Lane 1: Protein standard; Lane 2: Total protein; Lane 3: Soluble protein; Lane 4: Insoluble protein. Canine TSLP protein was detected in total protein and insoluble protein (as indicated by arrows).
Figure 2B:
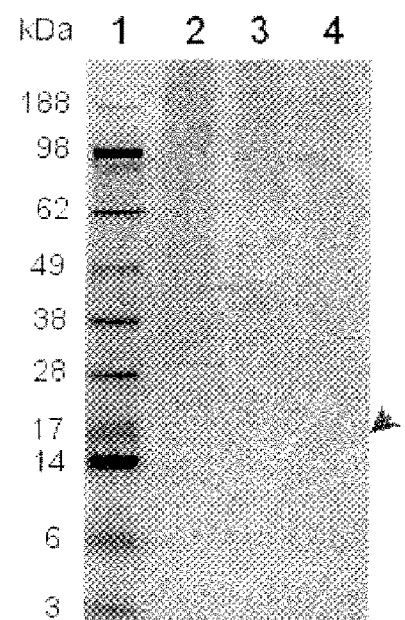
FIG. 2B illustrates Western blot analysis of protein from eukaryotic cell-free protein synthesis system expressing canine TSLP protein. The protein was reacted with a rat monoclonal antibodies specific for human TSLP. Lane 1: Protein standard; Lane 2: Total protein; Lane 3: Soluble protein; Lane 4: Insoluble protein. Canine TSLP protein was detected in total protein and insoluble protein (as indicated by arrows).

After Nco I and EcoR V digestion, the PCR products were inserted into Nco I and Sma I sites of vector pIVEX 1.3 WG (Roche Applied Sciences, Cat#3728803). This resulted in a plasmid containing the gene which encodes the mature canine TSLP fused with six His residues at the C-terminal end ("His6 tag"). The plasmid containing correct sequences of the inserts was named plasmid 1265-93.D. Plasmid 1265-93.D was used to express TSLP in the RTS Proteomaster Instrument according to manufacturer's recommendations (Roche Applied Sciences, Cat#3064859). As shown in FIG. 1, a band of @16 kDa was evident in lanes 2 and 4 (arrows). Western blot experiments (FIGS. 2A & 2B) show that this band reacted specifically with anti-His tag antibody (FIG. 2A) and a rat monoclonal antibody specific for human TSLP (FIG. 2B).

Example 3

Production of Canine TSLP from Host Cells

To express recombinant TSLP protein in *E. coli*, the nucleotide sequence encoding cTSLP (i.e., TSLP lacking nucleotides encoding the signal sequence) was amplified by PCR using plasmid 1265-66C as a template together with a forward primer and reverse primers that contain NcoI and Hind III site respectively:

```
Forward Primer
                                       (SEQ ID NO:6)
5'-AATAATCCATGGCATACAATTTCATTGACTGTGAC-3'

Reverse Primer
                                       (SEQ ID NO:7)
5'-ACATAAAAGCTTTGAAATGCGACTGAAACGACG-3'
```

Figure 3A:
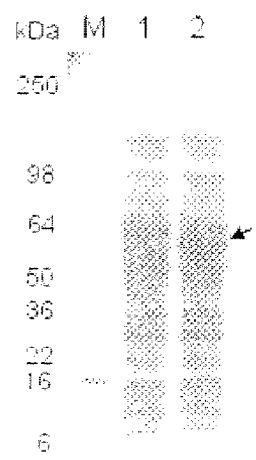
FIG. 3A illustrates the expression and purification of TSLP from E. coli host cells, and shows a band of @ 61 kd that is present in the soluble E. coli fraction that represents a fusion between canine TSLP and the fusion partner GST protein and a 6 histidine residue tag. "M" indicates the protein standard (same in all of FIGS. 3A-3D). Lane 1 and lane 2 are soluble fractions of E. coli B121(DE3)pLysS containing plasmid 1265-93B without and with IPTG induction, respectively. Arrow indicates the GST-TSLP-His fusion protein band (same in all of FIGS. 3A-3D).
Figure 3B:
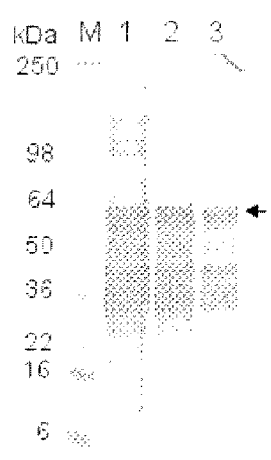
FIG. 3B shows that the GST-TSLP-His tagged fusion protein can be purified by glutathione Sepharose 4B resin. Lane 1 to 3 represents different elution fractions of Glutathion Sepharose 4B resin.
Figure 3C:
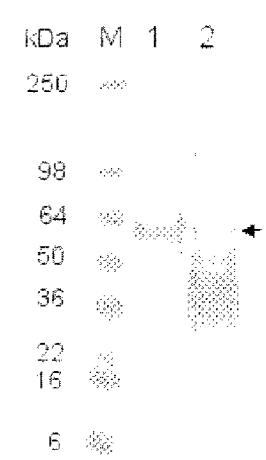
FIG. 3C shows that the fusion protein of lane B can be further purified using Ni-NTA resin. This figure illustrates the re-purification of GST-TSLP-His fusion protein after Glutathione Sepharose 4B purification by Ni-NTA resin. Lane 1 is the flow through, lane 2 is elecution of Ni-NTA resin.
Figure 3D:
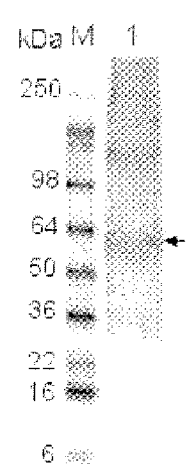
FIG. 3D illustrates a Western blot of GST-TSLP-His fusion protein and confirms that that the fusion protein is recognized by an anti-GST antibody (GE Health Care Cat No. 27457701).

After Nco I and Hind III digestion, the PCR products were inserted into NcoI/HindIII sites of pET42b(+) expression vector (Novagen). This process produced a plasmid which encodes the mature cTSLP fused with GST tag at the N terminus and a 6×His tag at the C terminus. The plasmid containing correct sequences of the insert was named as 1265-938. Expression of the GST-TSLP-His fusion protein was carried out in *E. coli* BL21 (DE3)/pLysS which contains the T7 RNA polymerase gene under the control of the isopropyl-β-D-thiogalactopyranoside (IPTG)-inducible lacUV5 promoter. *E. coli* cells carrying plasmid 1265-93B were grown at 30° C. to an O.D. 600 of 0.6 and then protein expression was induced by the addition of 0.5 mM IPTG and further incubation at 30° C. for 2 hours. SDS-PAGE displays a protein band (arrow) with the correct size (~61 kDa) present in the soluble *E. coli* fraction (FIG. 3A). Western blot shows that the expressed protein reacts with anti-GST antibody (FIG. 3D). The GST-TSLP-His protein can be purified by Glutathione Sepharose 4B resin (FIG. 3B). After additional purification by Ni-NTA resin, the majority of the GST-TSLP protein was contained in the column flow through (FIG. 3C).

Example 4

Immunofluorescent Detection of Canine TSLP

The expression of canine TSLP protein in canine skin and tonsil tissues was determined by immunohistochemistry ("IHC") using rabbit polyclonal antibodies raised against human TSLP protein. Immunohistochemistry was carried out on paraffin-embedded tissue blocks obtained from normal dog skin injected with saline as well as skin of dogs diagnosed with various skin diseases including atopic dermatitis, cutaneous lupus erythematosus, erythema multiforme, and junctional epidermolysis bullosa. Additionally, TSLP protein expression was determined in frozen tonsil tissues from two dogs. The procedure for determining TSLP expression by IHC is as follows:

I. Preparation of Sections:
1. Paraffin blocks with embedded skin samples were sectioned at a thickness of 5-7 microns and mounted on slides treated with poly-L-Lysine to promote adhesion.
2. Sections were de-paraffinized with xylene and rehydrated with serial ethanol solutions.
3. Antigen retrieval was carried out in citrate buffer [10 mM sodium citrate containing Tween-20 at a concentration of 0.5 ml/liter for 25 min using laboratory microwave to reach about 99-100° C.]. This is a process that recovers the antigenicity of tissue sections that are masked during the paraffin-embedding process.

II. Immunostaining:
1. Sections were incubated in 10% normal donkey serum diluted in phosphate buffer solution (PBS) for 1 hr at room temperature to reduce non-specific binding of the antibody.
2. Excess serum was gently removed, and the sections covered with rabbit antibody (1:100) diluted in PBS and incubated either at room temperature for 1 hour or overnight at 4° C. in a humidity chamber.
3. Sections were then rinsed twice for 5 minutes in PBS, with gentle shaking.
4. Excess PBS was gently removed and sections covered with biotinylated donkey anti-rabbit IgG antibody diluted 1:5000 in PBS for 30 minutes at room temperature in the humidity chamber.
5. Sections were then rinsed twice for 5 minutes in PBS, with gentle shaking.
6. Excess PBS was removed and the sections incubated for 30 min at room temperature in Streptavidin-fluorescein isothiocyanate (Streptavidin-FITC) conjugate in PBS at a concentration of 5 microgram/ml.

7. Sections were then rinsed twice for 5 minutes in PBS, shaking gently.
8. The sections were then counterstained with hemotoxylin for 2-3 min.
9. The sections were then examined under fluorescent microscope.
10. Pertinent images were photographed.
11. Experimental controls included omission of the primary anti-TSLP antibodies, or replacing the primary anti-TSLP antibody with normal rabbit antibodies.

Table 1, below, summarizes the results of the IHC experiments.

TABLE 1

Immunohistochemistry with rabbit anti-human TSLP Conducted on paraffin-embedded blocks of skin tissue from dogs with various skin diseases.

| Disease condition (Total number of blocks) | Positive blocks | Negative blocks |
| --- | --- | --- |
| AD lesional skin (* n = 10) | 8 | 2 |
| Normal skin injected with PBS (n = 5) | 1 | 4 |
| Junctional epidermolysis bullosa (n = 2) | 2 | 0 |
| Canine cutaneous lupus erythematsus (n = 3) | 0 | 3 |
| Erythema multiforme (n = 3) | 2 | 1 |

* n = the number of animals.

TSLP expression was detected in 80% of skin tissues from dogs diagnosed with AD, but only in 20% of normal skin tissues injected with saline. TSLP was also detected in 66% and 100% of tissues from dogs with *Erythema multifomre* and dogs with the genetic skin disease, junctional epidermolysis bullosa; respectively. There was no expression of TSLP protein in skin tissues from dogs with cutaneous *lupus erythematusus*. In paraffin-embedded skin tissues, the expression of TSLP was detected in sweat glands. Expression of TSLP in frozen canine tonsil tissue was detected in the stratified squamous epithelium and associated salivary glands. An example of positive IHC staining in dog skin samples is shown in FIG. 4 which represents paraffin-embedded skin tissue samples from a dog diagnosed with atopic dermatitis.

Example 6

Immunoperoxidase Detection of Canine TSLP

The expression of canine TSLP protein in paraffin-embedded tissue blocks prepared from skin of dogs diagnosed with atopic dermatitis was also determined by immunohistochemistry using immunoperoxidase staining as the detection method. In this method, an epitope-specific rat monoclonal antibody which was raised against human TSLP protein was used as the primary antibody. The procedure for determining TSLP expression by immunoperoxidase staining was as follows:

Special Reagents
Normal newborn calf serum: #N-4762 Sigma
Paraffin-embedded skin tissue
Primary antibody: Rat anti-human TSLP mAb rat IgG2a
Secondary antibody: Rabbit anti-rat IgG (biotinylated): BA-4000 Vector Lab. Burlingame, Calif.
Detection reagent: Streptavidin-HRP: #43-8323 Zymed Labs. San Francisco Calif.
AEC substrate Kit: Biogenex #HK129-5K San Ramon, Calif.
1. Section specimen 4-6 um.
2. Air dry 10 min. room temp.
3. Fix 10 min. in acetone.
4. Rinse in PBS (0.01 Phosphate Buffered Saline) 3 min.
5. Quench by incubation in 0.3% hydrogen peroxide with 0.1% sodium azide for 7-10 min.
6. Rinse 5 min. PBS.
7. Block sections with 1% Normal newborn calve serum 20 minutes in moist chamber.
8. Drain slides and apply primary antibody at 1:100 dilution for 2 hrs, at room temperature.
9. Rinse 5 min.
10. Apply secondary antibody (Rabbit anti-rat IgG @1-400) 30 minutes in moist chambers at room temperature.
11. Rinse 5 min.
12. Drain and apply detection reagent (Streptavidin-HRP @1:400) for 30 min at room temperature
13. Rinse 2×5 minutes.
14. Apply AEC 2.5 min. Adjust according to desired staining intensity and background.
15. Counterstain with Hematoxylin and mount.

Figure 5A:
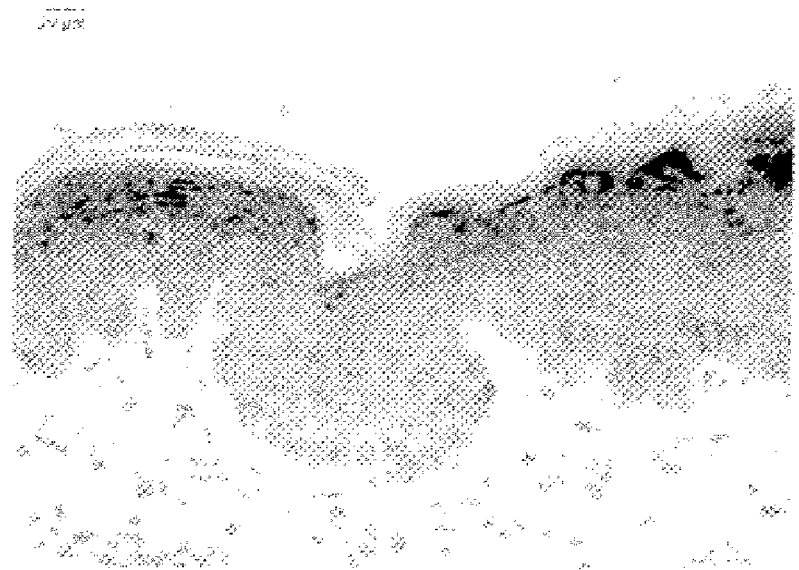
FIG. 5A illustrates immunoperoxidase staining of a section from a paraffin-embedded block of lesional skin tissue obtained from a dog that was diagnosed with atopic dermatitis. In this section, there is a diffuse staining [dark areas] of epidermal area of skin specimen by rat anti-human TSLP monoclonal antibody.
Figure 5B:
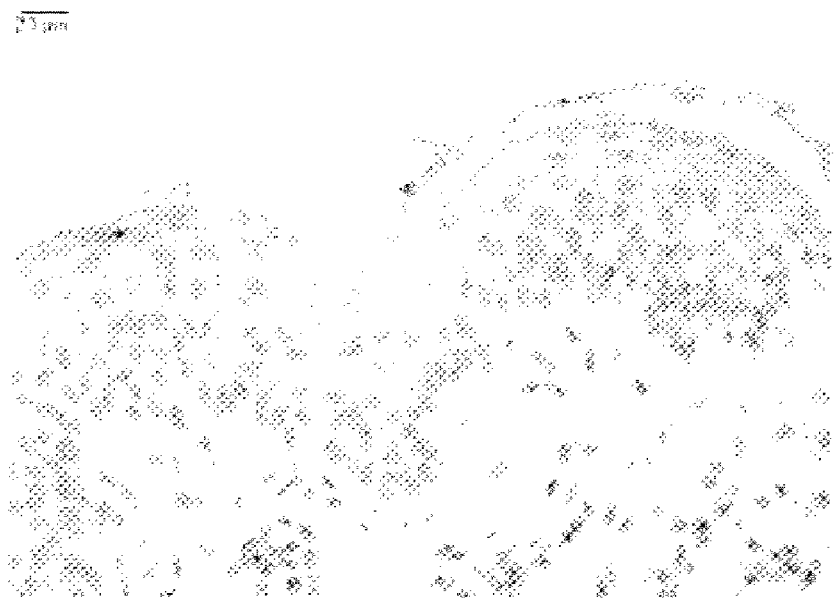
FIG. 5B illustrates a control section. The section was from a paraffin-embedded block of lesional skin tissue obtained from a dog that was diagnosed with atopic dermatitis that was treated only with a phosphate buffered control.

A set of canine skin tissues from dogs with AD was tested by IHC using an epitope specific canine TSLP antibody. The results shown in FIG. 5 indicate that this antibody reacts with a molecule that shares antigenic epitopes with human TSLP. The staining of canine AD skin specimens was strong in areas of chronic inflammation where the epidermis is thickened. This pattern is consistent with what is known about the location of TSLP expression in human AD skin lesions and further suggests the recognized molecule in canine skin AD lesions is canine TSLP. There was no staining observed with either PBS or a different rat monoclonal specific for a different protein (a lymphocyte protein).

Example 7

Epitope Mapping of Canine TSLP

In order to identify epitopes on canine TSLP that are useful for inclusion in a vaccine capable of neutralizing TSLP activity, a set of overlapping peptides based on the canine TSLP protein sequence were synthesized and tested for their ability to react with a neutralizing anti-human TSLP monoclonal antibody. For this purpose a set of overlapping peptides each 15 amino acid long and off set by two amino acids were synthesized on pins at MIMOTOPES (Minneapolis, Minn.). The sequences of these peptides are listed in Table 2. Peptides 1-57 were synthesized with an amidated terminus in the configuration NH2-PEPTIDE-PIN. Peptides 58-94 (duplicates of parent peptides 1-37) were made with an acytelated terminus in the configuration ACETYL-PEPTIDE-PIN.

Figure 6:
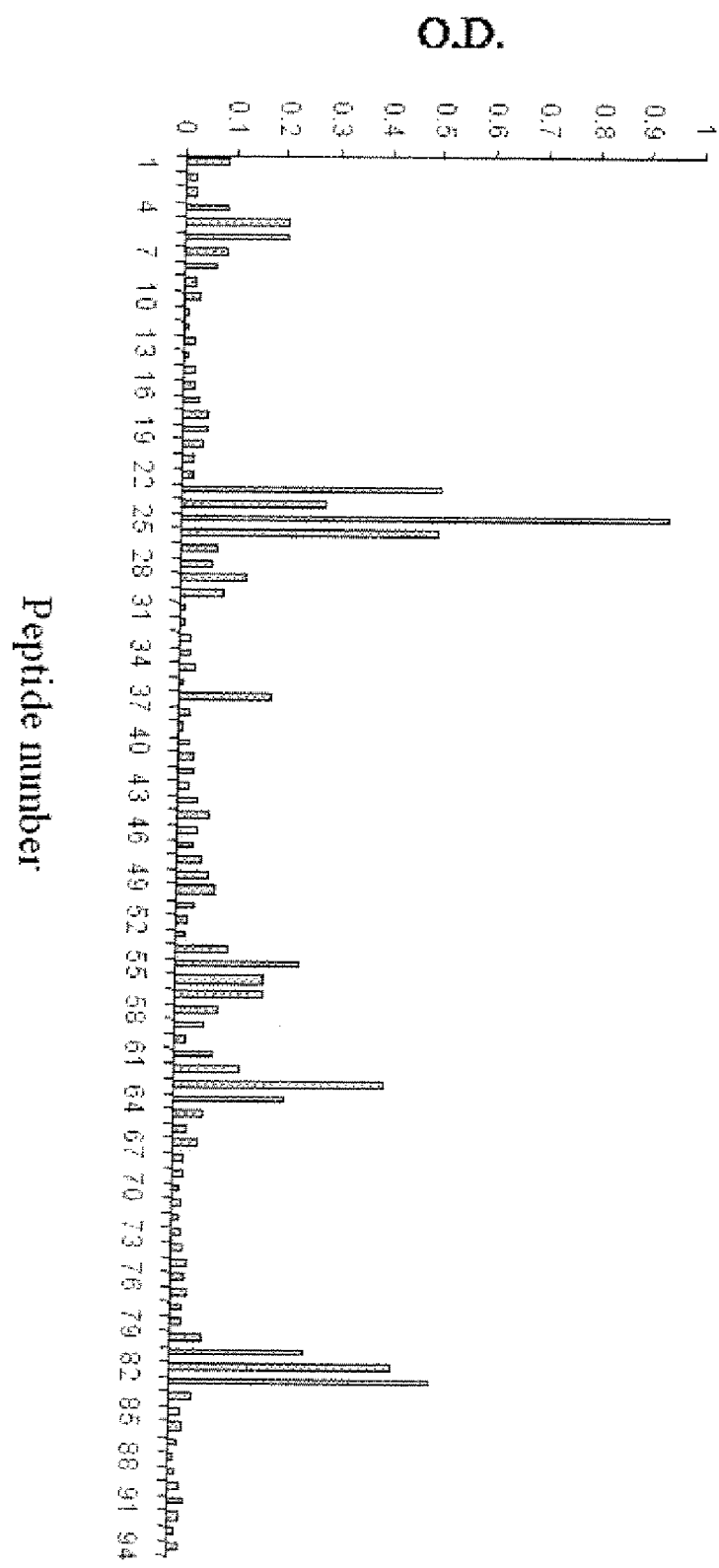
FIG. 6 illustrates epitope mapping of canine TSLP protein with rat anti-human TSLP monoclonal antibody. Peaks of particular interest are from epitope numbers 22-26 (SEQ ID NOs 29-33). Epitopes 22-26 were also run with N-terminal derivatization (peak 55 and up), to confirm that the binding epitope does not require the N-terminal residue.

The pins carrying the peptide listed in Table 2 were tested in an ELISA assay format according to manufacturer's recommended procedures (Mimotopes, Minneapolis, Minn.). As shown in FIG. 6, peptide #25 (epitope 25) with the amino acid sequence NH2-ARIERLTLHRIRGCA (SEQ ID NO: 32) had the highest reactivity against the PAB100 monoclonal antibody. A comparison of this peptide sequence with a corresponding putative human TALK peptide sequence is shown in FIG. 7.

TABLE 2

Canine TSLP peptides used for epitope mapping

| EPITOPE NUMBER | | SEQ ID NOs: |
|---|---|---|
| 1 | YNFIDCDFEKIRWKY | 8 |
| 2 | FIDCDFEKIRWKYQE | 9 |
| 3 | DCDFEKIRWKYQEVI | 10 |
| 4 | DFEKIRWKYQEVIYQ | 11 |
| 5 | EKIRWKYQEVIYQAL | 12 |
| 6 | IRWKYQEVIYQALEK | 13 |
| 7 | WKYQEVIYQALEKYM | 14 |
| 8 | YQEVIYQALEKYMDG | 15 |
| 9 | EVIYQALEKYMDGTR | 16 |
| 10 | IYQALEKYMDGTRST | 17 |
| 11 | QALEKYMDGTRSTEF | 18 |
| 12 | LEKYMDGTRSTEFSH | 19 |
| 13 | KYMDGTRSTEFSHPV | 20 |
| 14 | MDGTRSTEFSHPVYC | 21 |
| 15 | GTRSTEFSHPVYCAN | 22 |
| 16 | RSTEFSHPVYCANPP | 23 |
| 17 | TEESEPVYCANPPDC | 24 |
| 18 | FSHPVYCANPPDCLA | 25 |
| 19 | HPVYCANPPDCLARI | 26 |
| 20 | VYCANPPDCLARIER | 27 |
| 21 | CANPPDCLARIERLT | 28 |
| 22 | NPPDCLARIERLTLH | 29 |
| 23 | PDCLARIERLTLHRI | 30 |
| 24 | CLARIERLTLHRIRG | 31 |
| 25 | ARTERLTLHRIRGCA | 32 |
| 26 | IERLTLHRIRGCASG | 33 |
| 27 | RLTLHRIRGCASGAR | 34 |
| 28 | TLHRIRGCASGAREA | 35 |
| 29 | HRIRGCASGAREAFA | 36 |
| 30 | IRGCASGAREAFAEG | 37 |
| 31 | GCASGAREAFAEGTV | 38 |
| 32 | ASGAREAFAEGTVAA | 39 |
| 33 | GAREAFAEGTVAALA | 40 |
| 34 | REAFAEGTVAALAAE | 41 |
| 35 | AFAEGTVAALAAECP | 42 |
| 36 | AEGTVAALAAECPGY | 443 |
| 37 | GTVAALAAECPGYAA | 44 |
| 38 | VAALAAECPGYAAAP | 45 |
| 39 | ALLAECPGYAAAPIN | 46 |
| 40 | AAECPGYAAAPINNT | 47 |
| 41 | ECPGYAAAPINNTQA | 48 |
| 42 | PGYAAAPINNTQAKK | 49 |
| 43 | YAAAPINNTQAKKKR | 50 |
| 44 | AAPINNTQAKKKRKK | 51 |
| 45 | PINNTQAKKKRKKRG | 52 |
| 46 | NNTQAKKKRKKRGVT | 53 |
| 47 | TQAKKKRKKGVTTN | 54 |
| 48 | AKKKRKKRGVTTNKC | 55 |
| 49 | KKRKKRGVTTNKCRE | 56 |
| 50 | RKKRGVTTNKCREQV | 57 |
| 51 | KRGVTTNKCREQVAH | 58 |
| 52 | GVTTNKCREQVAHLI | 59 |
| 53 | TTNKCREQVAHLIGL | 60 |
| 54 | NKCREQVAHLIGLWR | 61 |
| 55 | CREQVAHLIGLWRRF | 62 |
| 56 | EQVAHLIGLWRRFSR | 63 |
| 57 | VAHLIGLWRRFSRIS | 64 |
| 58 | YNFIDCDFEKIRWKY | 65 |
| 59 | FIDCDKEKIRWKYQE | 66 |
| 60 | DCDFEKIRWKYQEVI | 67 |
| 61 | DFEKIRWKYQEVIYQ | 68 |
| 62 | EKIRWKYQEVIYQAL | 69 |
| 63 | IRWKYQEVIYQALEK | 70 |
| 64 | WKYQEVIYQALEKYM | 71 |
| 65 | YQEVIYQALEKYMDG | 72 |
| 66 | EVIYQALEKYMDGTR | 73 |
| 67 | IYQALEKYMDGTRST | 74 |
| 68 | QALEKYMDGTRSTEF | 75 |
| 69 | LEKYMDGTRSTEFSH | 76 |
| 70 | MDGTRSTEFSHPVYC | 77 |
| 71 | KYMDGTRSTEFSHPV | 78 |
| 72 | GTRSTEFSHPVYCAN | 79 |
| 73 | RSTEFSHPVYCANPP | 80 |
| 74 | TEFSHPVYCANPPDC | 81 |

TABLE 2-continued

Canine TSLP peptides used for epitope mapping

| EPITOPE NUMBER | | SEQ ID NOs: |
|---|---|---|
| 75 | FSHEVYCANPPDCLA | 82 |
| 76 | HPVYCANPPDCLARI | 83 |
| 77 | VYCANPPDCLARIER | 84 |
| 78 | CANPPDCLARIERLT | 85 |
| 79 | NPPDCLARIERLTLH | 86 |
| 80 | PDCLARIERLTLHRI | 87 |
| 81 | CLARIERLTLHRIRG | 88 |
| 82 | ARIERLTLHRIRGCA | 89 |
| 83 | IERLTLHRIRGCASG | 90 |
| 84 | RLTLHRIRGCASGAR | 91 |
| 85 | TLHRIRGCASGAREA | 92 |
| 86 | HRIRGCASGAREAFA | 93 |
| 87 | IRGCASGAREAFAEG | 94 |
| 88 | GCASGAREAFAEGTV | 95 |
| 89 | ASGAREAFAEGTVAA | 96 |
| 90 | GAREAFAEGTVAALA | 97 |
| 91 | REAFAEGTVAALAAE | 98 |
| 92 | AFAEGTVAALAAECP | 99 |
| 93 | AEGTVAALAAECPGY | 100 |
| 94 | GTVAALAAECPGYAA | 101 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are hereby incorporated by reference in their entireties.

We claim:

1. An isolated thymic stromal lymphopoietin protein (TSLP) or an antigenic fragment thereof, wherein said TSLP protein comprises an amino acid sequence that has 90% or greater identity to the amino acid sequence of SEQ ID NO: 2, excluding the 28 amino acid residue signal sequence; and wherein said TSLP protein is cross reactive with an antibody raised against the canine TSLP comprising the amino acid of SEQ ID NO: 2.

2. The isolated TSLP of claim 1 wherein the TSLP binds to an epitope-specific canine TSLP antibody.

3. The isolated TSLP of claim 1 that is an isolated canine TLSP.

4. The isolated canine TSLP protein of claim 3 that comprises amino acid residues 29-155 of SEQ ID NO: 2.

5. An antigenic fragment of the isolated TSLP protein of claim 4, wherein said antigenic fragment comprises the amino acid sequence of SEQ ID NO:64.

6. An antigenic fragment of the isolated canine TSLP protein of claim 5, wherein said fragment further comprises an amino acid sequence selected from the group consisting of SEQ ID NOs: 8-63 and 65-101 or a combination of two or more thereof.

7. A composition comprising a pharmaceutically acceptable adjuvant and an effective amount of an immunogen selected from the group consisting of the TSLP protein of claim 1, an antigenic fragment of the TSLP protein, and combinations thereof.

8. A method of inducing anti-TSLP antibodies in a mammal comprising immunizing the mammal with an effective amount of the composition of claim 7.

9. A method of downregulating TSLP activity in a canine comprising immunizing the canine with an effective amount of the composition of claim 7.

10. A method of treating allergic symptoms in an atopic canine comprising immunizing a canine with an effective amount of the composition of claim 7.

11. The method of claim 10 wherein the allergic symptoms comprise allergic dermatitis or asthma.

12. The composition of claim 7 that further comprises an effective amount of a non-TSLP immunogen.

13. A recombinant thymic stromal lymphopoietin protein (TSLP) or an antigenic fragment thereof, wherein said TSLP protein corriprises an amino acid sequence that has 90% or greater identity to the amino acid sequence of SEQ ID NO: 2, excluding the 28 amino acid residue signal sequence; and wherein said TSLP protein is cross reactive with an antibody raised against the canine TSLP comprising the amino acid of SEQ ID NO: 2.

14. The recombinant TSLP of claim 13 wherein the TSLP binds to an epitope-specific canine TSLP antibody.

15. The recombinant TSLP of claim 13 that is a recombinant canine TLSP.

16. The recombinant canine TSLP protein of claim 3 that comprises amino acid residues 29-1 55 of SEQ ID NO: 2.

17. An antigenic fragment of the recombinant canine TSLP protein of claim 16, wherein said antigenic fragment comprises the amino acid sequence of SEQ ID NO:64.

18. An antigenic fragment of the recombinant canine TSLP protein of claim 17, wherein said fragment further comprises an amino acid sequence selected from the group consisting of SEQ ID NOs: 8-63 and 65-101 or a combination of two or more thereof.

* * * * *

UNITED STATES PATENT AND TRADEMARK OFFICE
CERTIFICATE OF CORRECTION

PATENT NO. : 7,718,772 B2
APPLICATION NO. : 11/954143
DATED : May 18, 2010
INVENTOR(S) : Jeanine D. Mattson et al.

It is certified that error appears in the above-identified patent and that said Letters Patent is hereby corrected as shown below:

Claim 16, Column 76, lines 1-2: Please replace

"The recombinant canine TSLP protein of claim 3 that comprises amino acid residues 29-1 55 of SEQ ID NO: 2."

with

--The recombinant canine TSLP protein of claim 15 that comprises amino acid residues 29-155 of SEQ ID NO: 2.--

Signed and Sealed this
Twenty-first Day of February, 2012

David J. Kappos
*Director of the United States Patent and Trademark Office*